(12) United States Patent
Pattillo

(10) Patent No.: US 12,127,575 B2
(45) Date of Patent: *Oct. 29, 2024

(54) ENHANCED AEROBIC FERMENTATION METHODS FOR PRODUCING EDIBLE FUNGAL MYCELIUM BLENDED MEATS AND MEAT ANALOGUE COMPOSITIONS

(71) Applicant: The Better Meat Co., West Sacramento, CA (US)

(72) Inventor: Augustus H. Pattillo, Atlanta, GA (US)

(73) Assignee: THE BETTER MEAT CO., West Sacramento, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/371,745

(22) Filed: Jul. 9, 2021

(65) Prior Publication Data

US 2022/0000159 A1     Jan. 6, 2022

Related U.S. Application Data

(63) Continuation of application No. 16/586,150, filed on Sep. 27, 2019, now Pat. No. 11,470,871, which is a
(Continued)

(51) Int. Cl.
| | | |
|---|---|---|
| A23L 31/00 | (2016.01) | |
| A23J 3/04 | (2006.01) | |

(Continued)

(52) U.S. Cl.
CPC ................. *A23L 31/00* (2016.08); *A23J 3/04* (2013.01); *A23J 3/14* (2013.01); *A23J 3/20* (2013.01);

(Continued)

(58) Field of Classification Search
CPC ......... A23L 31/00; A23K 50/40; A23K 10/12; A23J 3/227; A23J 3/20; C12N 1/14; C12P 21/00

(Continued)

(56) References Cited

U.S. PATENT DOCUMENTS

| | | |
|---|---|---|
| 1,822,227 A | 9/1931 | Lendrich et al. |
| 2,450,055 A | 9/1948 | Nord |

(Continued)

FOREIGN PATENT DOCUMENTS

| | | |
|---|---|---|
| AT | 101660 B | 7/1922 |
| CN | 1094258 A | 11/1994 |

(Continued)

OTHER PUBLICATIONS

Kim, K. et al. J. Sci. Food Agric. 91: 1561-1568 (Year: 2011).*

(Continued)

*Primary Examiner* — Jyoti Chawla
(74) *Attorney, Agent, or Firm* — McDonnell Boehnen Hulbert & Berghoff LLP

(57) ABSTRACT

Provided herein are shelf-stable protein food ingredients, food products comprising the shelf-stable protein food ingredients, methods of their production, and methods of their use. The shelf-stable protein food ingredients comprise cultured fungal biomass and a limited amount of water. Advantageously, the shelf-stable protein food ingredients can be stored, transported, and delivered within the food supply.

46 Claims, 6 Drawing Sheets

Related U.S. Application Data continuation of application No. 16/578,099, filed on Sep. 20, 2019, now Pat. No. 11,058,137.

(60) Provisional application No. 62/733,925, filed on Sep. 20, 2018.

(51) Int. Cl.
| | | |
|---|---|---|
| A23J 3/14 | (2006.01) | |
| A23J 3/20 | (2006.01) | |
| A23J 3/22 | (2006.01) | |
| A23K 10/12 | (2016.01) | |
| A23K 50/40 | (2016.01) | |
| A23L 13/40 | (2023.01) | |
| C12N 1/14 | (2006.01) | |
| C12P 21/00 | (2006.01) | |

(52) U.S. Cl.
CPC .............. *A23J 3/227* (2013.01); *A23K 10/12* (2016.05); *A23K 50/40* (2016.05); *A23L 13/424* (2016.08); *A23L 13/46* (2016.08); *C12N 1/14* (2013.01); *C12P 21/00* (2013.01)

(58) Field of Classification Search
USPC .......................................................... 426/7
See application file for complete search history.

(56) References Cited

U.S. PATENT DOCUMENTS

| | | |
|---|---|---|
| 2,693,664 A | 11/1954 | Szuecs |
| 2,693,665 A | 11/1954 | Humfeld et al. |
| 2,761,246 A | 9/1956 | Szuecs |
| 2,928,210 A | 3/1960 | Cirillo et al. |
| 3,086,320 A | 4/1963 | Heinemann et al. |
| 3,530,551 A | 9/1970 | Haes et al. |
| 3,749,584 A | 7/1973 | Kurtzman et al. |
| 3,810,997 A | 5/1974 | Chien |
| 3,885,048 A | 5/1975 | Liggett |
| 3,912,825 A | 10/1975 | Spicer et al. |
| 3,937,654 A | 2/1976 | Solomons et al. |
| 3,969,189 A | 7/1976 | Kobayashi et al. |
| 3,998,975 A | 12/1976 | Liepa et al. |
| 4,056,638 A | 11/1977 | Huang et al. |
| 4,061,781 A | 12/1977 | Solomons et al. |
| 4,071,973 A | 2/1978 | Iizuka et al. |
| 4,154,862 A | 5/1979 | Guadagni et al. |
| 4,212,947 A | 7/1980 | Torev |
| 4,265,915 A | 5/1981 | MacLennan et al. |
| 4,367,240 A | 1/1983 | Maclennan et al. |
| 4,555,485 A | 11/1985 | Marsh |
| 4,590,160 A | 5/1986 | Nishihashi et al. |
| 4,800,093 A | 1/1989 | Hogan et al. |
| 4,891,220 A | 1/1990 | Donzis |
| 4,938,972 A | 7/1990 | Moo-Young et al. |
| 5,532,148 A | 7/1996 | Datta et al. |
| 5,631,292 A | 5/1997 | Kurtz et al. |
| 5,934,012 A | 8/1999 | Holtz et al. |
| 6,045,834 A | 4/2000 | Howes et al. |
| 6,254,901 B1 | 7/2001 | Ono |
| 6,265,012 B1 | 7/2001 | Shamil |
| 6,277,396 B1 | 8/2001 | Dente |
| 6,383,799 B1 | 5/2002 | Wasser et al. |
| 6,416,978 B1 | 7/2002 | Lee et al. |
| 6,476,003 B1 | 11/2002 | Jordan et al. |
| 6,490,824 B1 | 12/2002 | Intabon et al. |
| 6,558,943 B1 | 5/2003 | Li et al. |
| 6,569,475 B2 | 5/2003 | Song |
| 7,045,160 B1 | 5/2006 | de Haan et al. |
| 7,745,189 B2 | 6/2010 | Akin et al. |
| 7,855,059 B2 | 12/2010 | Wenger et al. |
| 7,939,671 B2 | 5/2011 | Li et al. |
| 8,313,929 B2 | 11/2012 | Van Wezel et al. |
| 8,343,741 B2 | 1/2013 | Liu et al. |
| 8,481,295 B2 | 7/2013 | van Leeuwen et al. |
| 8,672,245 B2 | 3/2014 | Finnigan et al. |
| 9,068,171 B2 | 6/2015 | Kelly et al. |
| 9,079,786 B2 | 7/2015 | Van Leeuwen et al. |
| 9,289,003 B2 | 3/2016 | Kringelum et al. |
| 9,301,539 B2 | 4/2016 | Appel et al. |
| 9,526,267 B2 | 12/2016 | Anderson et al. |
| 9,572,363 B2 | 2/2017 | Langan et al. |
| 9,943,096 B2 | 4/2018 | Fraser et al. |
| 10,010,103 B2 | 7/2018 | Soni et al. |
| 10,154,627 B2 | 12/2018 | McIntyre et al. |
| 10,370,636 B2 | 8/2019 | Van Hee |
| 10,617,697 B2 | 4/2020 | Levanon et al. |
| 10,661,320 B2 | 5/2020 | Huang et al. |
| 10,829,420 B2 | 11/2020 | Ren et al. |
| 11,032,982 B2 | 6/2021 | Ross et al. |
| 11,058,137 B2 | 7/2021 | Pattillo |
| 11,554,990 B2 | 1/2023 | Ren et al. |
| 11,751,596 B2 | 9/2023 | Huggins et al. |
| 2002/0082418 A1 | 6/2002 | Ikewaki |
| 2002/0096473 A1 | 7/2002 | Ferro et al. |
| 2002/0137155 A1 | 9/2002 | Wasser et al. |
| 2002/0177576 A1 | 11/2002 | McGregor et al. |
| 2003/0208796 A1 | 11/2003 | Song |
| 2004/0009143 A1 | 1/2004 | Golz-Berner et al. |
| 2004/0035047 A1 | 2/2004 | Hwang et al. |
| 2004/0197461 A1 | 10/2004 | Finnigan et al. |
| 2004/0211721 A1 | 10/2004 | Stamets |
| 2005/0180989 A1 | 8/2005 | Matsunaga |
| 2005/0255126 A1 | 11/2005 | Tsubaki et al. |
| 2005/0273875 A1 | 12/2005 | Elias |
| 2006/0014267 A1 | 1/2006 | Cleaver et al. |
| 2006/0068056 A1 | 3/2006 | Sakamoto et al. |
| 2006/0134294 A1 | 6/2006 | McKee |
| 2006/0280753 A1 | 12/2006 | McNeary |
| 2007/0160726 A1 | 7/2007 | Fujii |
| 2008/0031892 A1 | 2/2008 | Kristiansen |
| 2008/0038404 A1 | 2/2008 | Brunstedt et al. |
| 2008/0057162 A1 | 3/2008 | Brucker et al. |
| 2008/0107783 A1 | 5/2008 | Anijs et al. |
| 2008/0171104 A1 | 7/2008 | Zhu et al. |
| 2008/0193595 A1 | 8/2008 | De Vuyst et al. |
| 2008/0226788 A1 | 9/2008 | Chang et al. |
| 2008/0264858 A1 | 10/2008 | Stamets |
| 2008/0274234 A1 | 11/2008 | Miller |
| 2008/0296223 A1 | 12/2008 | Hiromoto |
| 2008/0299645 A1 | 12/2008 | Holliday |
| 2009/0047236 A1 | 2/2009 | Stamets |
| 2009/0053363 A1 | 2/2009 | An |
| 2009/0098244 A1 | 4/2009 | Schatzmayr et al. |
| 2009/0104310 A1 | 4/2009 | Nakajima |
| 2009/0130138 A1 | 5/2009 | Stamets |
| 2009/0148558 A1 | 6/2009 | Kim et al. |
| 2009/0220645 A1 | 9/2009 | Martinez |
| 2009/0280212 A1 | 11/2009 | Sugimoto et al. |
| 2010/0055241 A1 | 3/2010 | Nakano et al. |
| 2010/0183765 A1 | 7/2010 | Laan Van Der et al. |
| 2010/0203189 A1 | 8/2010 | Holliday |
| 2010/0203194 A1 | 8/2010 | Salminen et al. |
| 2010/0213293 A1 | 8/2010 | Finnigan et al. |
| 2010/0221385 A1 | 9/2010 | Matsui et al. |
| 2010/0227039 A1 | 9/2010 | Ungureanu et al. |
| 2010/0239711 A1 | 9/2010 | Li |
| 2010/0266726 A1 | 10/2010 | Ogura et al. |
| 2010/0284944 A1 | 11/2010 | Ungureanu et al. |
| 2010/0316763 A1 | 12/2010 | Choi et al. |
| 2011/0008384 A1 | 1/2011 | Stamets |
| 2011/0306107 A1 | 2/2011 | Kalisz et al. |
| 2011/0052758 A1 | 3/2011 | Greiner-Stoeffele |
| 2011/0070332 A1 | 3/2011 | Bernaert et al. |
| 2011/0081448 A1 | 4/2011 | Dunphy et al. |
| 2011/0086138 A1 | 4/2011 | Jia et al. |
| 2011/0091579 A1 | 4/2011 | Hausman |
| 2011/0123675 A1 | 5/2011 | Bernaert et al. |
| 2011/0189220 A1 | 8/2011 | Yang |
| 2011/0200551 A1 | 8/2011 | Stamets |
| 2011/0206721 A1 | 8/2011 | Nair |
| 2011/0229616 A1 | 9/2011 | Anijs et al. |
| 2011/0262593 A1 | 10/2011 | Binggeli et al. |
| 2011/0268980 A1 | 11/2011 | Kalisz et al. |

(56) References Cited

U.S. PATENT DOCUMENTS

| | | |
|---|---|---|
| 2012/0027889 A1 | 2/2012 | Portella |
| 2012/0034339 A1 | 2/2012 | Giuliani et al. |
| 2012/0034344 A1 | 2/2012 | Menon et al. |
| 2012/0082754 A1 | 4/2012 | Holliday |
| 2012/0100249 A1 | 4/2012 | Laan et al. |
| 2012/0128823 A1 | 5/2012 | Camu et al. |
| 2012/0171308 A1 | 7/2012 | Da Luz Moreira et al. |
| 2012/0177781 A1 | 7/2012 | Hayashi |
| 2012/0180167 A1 | 7/2012 | Usami |
| 2012/0190093 A1 | 7/2012 | Fukuda |
| 2012/0231114 A1 | 9/2012 | Bezerra De Oliveira et al. |
| 2012/0244254 A1 | 9/2012 | Takahashi |
| 2012/0321744 A1 | 12/2012 | Chhun et al. |
| 2013/0078192 A1 | 3/2013 | Backes et al. |
| 2013/0142691 A1 | 6/2013 | Ozasa |
| 2013/0142820 A1 | 6/2013 | Fares et al. |
| 2013/0142903 A1 | 6/2013 | Duan et al. |
| 2013/0209608 A1 | 8/2013 | Berends et al. |
| 2013/0209609 A1 | 8/2013 | Moreno et al. |
| 2013/0216654 A1 | 8/2013 | Yu et al. |
| 2013/0337114 A1 | 12/2013 | Binggeli et al. |
| 2014/0065263 A1 | 3/2014 | Kelly et al. |
| 2014/0105928 A1 | 4/2014 | Stamets |
| 2014/0170264 A1 | 6/2014 | Kelly et al. |
| 2014/0302560 A1 | 10/2014 | Kelly |
| 2014/0342036 A1 | 11/2014 | Appel et al. |
| 2015/0140098 A1 | 5/2015 | Van Den Elshout et al. |
| 2015/0257405 A1 | 9/2015 | Kelly et al. |
| 2015/0257406 A1 | 9/2015 | Kelly et al. |
| 2015/0272155 A1 | 10/2015 | Kelly et al. |
| 2015/0296834 A1 | 10/2015 | Geistlinger |
| 2015/0342138 A1 | 12/2015 | Bayer et al. |
| 2016/0073671 A1 | 3/2016 | Geistlinger |
| 2016/0120201 A9 | 5/2016 | Kelly et al. |
| 2016/0249660 A1 | 9/2016 | Langan et al. |
| 2016/0312247 A1* | 10/2016 | Lennartsson ......... A23K 50/80 |
| 2017/0295837 A1 | 10/2017 | Soni et al. |
| 2018/0014567 A1 | 1/2018 | Finnigan et al. |
| 2018/0064148 A1 | 3/2018 | Langan et al. |
| 2018/0303044 A1 | 10/2018 | Soni et al. |
| 2019/0059431 A1* | 2/2019 | Kozubal ............... C12M 23/34 |
| 2019/0069575 A1 | 3/2019 | Shigeta et al. |
| 2019/0307157 A1 | 10/2019 | Kozubal et al. |
| 2019/0373934 A1 | 12/2019 | Huggins et al. |
| 2019/0373935 A1 | 12/2019 | Huggins et al. |
| 2020/0024577 A1 | 1/2020 | Carlton et al. |
| 2020/0093155 A1 | 3/2020 | Pattillo |
| 2020/0093167 A1 | 3/2020 | Pattillo |
| 2020/0268031 A1 | 8/2020 | Macur et al. |
| 2021/0024428 A1 | 1/2021 | Ren et al. |
| 2021/0059287 A1 | 3/2021 | Kozubal et al. |
| 2021/0127601 A9 | 5/2021 | Kaplan-Bie et al. |
| 2021/0171896 A1 | 6/2021 | Harney et al. |
| 2021/0337827 A1 | 11/2021 | Whiteley et al. |
| 2022/0000159 A1 | 1/2022 | Pattillo |
| 2022/0000162 A1 | 1/2022 | Hüttner |
| 2022/0117276 A1 | 4/2022 | Pattillo |
| 2022/0117282 A1 | 4/2022 | Pattillo |
| 2022/0225653 A1 | 7/2022 | Soni et al. |
| 2022/0322617 A1 | 10/2022 | Soni et al. |
| 2023/0180807 A1 | 6/2023 | Huggins et al. |
| 2023/0180808 A1 | 6/2023 | Huggins et al. |
| 2023/0371569 A1 | 11/2023 | Huggins et al. |
| 2024/0099348 A1 | 3/2024 | Huggins et al. |

FOREIGN PATENT DOCUMENTS

| | | |
|---|---|---|
| CN | 101899399 A | 12/2010 |
| CN | 101579103 B | 8/2012 |
| CN | 102860541 A | 1/2013 |
| CN | 103229888 A | 8/2013 |
| CN | 103987271 A | 8/2014 |
| CN | 107072245 A | 8/2017 |
| CN | 107072246 A | 8/2017 |
| CN | 108026559 A | 5/2018 |
| CN | 110106090 A | 8/2019 |
| DE | 4341316 A1 | 6/1995 |
| DK | 3292769 T3 | 7/2019 |
| EP | 0986960 A1 | 3/2000 |
| EP | 2835058 A1 | 2/2015 |
| EP | 3131406 | 2/2017 |
| EP | 3292769 B1 | 4/2019 |
| GB | 1537173 A | 12/1976 |
| GB | 2059243 A | 4/1981 |
| GB | 2137226 A | 10/1984 |
| GB | 2120534 B | 1/1986 |
| JP | S59135840 A | 8/1984 |
| JP | S61219340 A | 9/1986 |
| JP | S6291161 A | 4/1987 |
| JP | H10179089 | 7/1998 |
| JP | H 11346657 A | 12/1999 |
| JP | 2000316512 A | 11/2000 |
| JP | 2003333998 A | 11/2003 |
| JP | 2005-0027540 A | 2/2005 |
| JP | 4126037 B2 | 7/2008 |
| KR | 100762848 B1 | 10/2007 |
| KR | 1020190139187 | 12/2019 |
| KR | 1020190162768 | 12/2019 |
| WO | 2020/061502 A1 | 3/2010 |
| WO | 2017/068012 | 4/2017 |
| WO | WO 2017/151684 A1 | 9/2017 |
| WO | WO 2017/208255 | 12/2017 |
| WO | 2018/075112 A1 | 4/2018 |
| WO | 2019/121697 A1 | 6/2019 |
| WO | WO 2019/237059 A1 | 12/2019 |
| WO | 2020/074782 A1 | 4/2020 |
| WO | WO 2020/106743 A1 | 5/2020 |
| WO | WO 2021/163215 A1 | 8/2021 |
| WO | WO 2021/163216 A1 | 8/2021 |

OTHER PUBLICATIONS

Hung, Yung-Tse, Howard H. Lo, Adel Awad, and Hana Salman. "Potato wastewater treatment." In Handbook of Industrial and Hazardous Wastes Treatment, pp. 894-951. CRC Press, 2004.

"The Original Mycoprotein." Downloaded on May 11, 2022 from eniferbio. fi/the-original-mycoprotein/. Article dated Feb. 8, 2022, 13 pages.

EniferBio. "eniferBio teams up with Tereos to provide sustainable PEKILO@ protein for Skretting's feeding trials", YouTube, May 4, 2021 (video online). [Retrieved from the internet on May 11, 2022, <https://youtu.be/7RVNdUZkglw>].

EniferBio. "The world's first mycoprotein plant—The Pekilo® plant in Jamsankoski, Finland", YouTube, Apr. 10, 2022 (vdieo online). [Retrieved from the internet on May 11, 2022, <https://youtu.be/hkwWNxKa14Q>].

EniferBio. "The PEKILOR Process", YouTube, Mar. 8, 2022 (video online). [Retrieved from the internet on May 11, 2022, <https://youtu.be/OrU8lhlZHuU>].

U.S. Appl. No. 17/739,725, filed May 9, 2022.

Non-Final Office Action and pending claims, U.S. Appl. No. 17/561,312, dated Apr. 29, 2022, 14 pages.

Non-Final Office Action and pending claims, U.S. Appl. No. 17/561,322 dated Mar. 28, 2022, 14 pages.

International Search Report and Written Opinion, Application No. PCT/US2022/028320, dated Sep. 21, 2022, 14 pages.

Asgar et al.: "Nonmeat Protein Alternatives as Meat Extenders and Meat Analogs", Comprehensive Reviews in Food Science and Food Safety, vol. 9, No. 5, Sep. 1, 2010 (Sep. 1, 2010), pp. 513-529, XP55005273, ISSN: 1541-4337, DOI: 10.1111/j.1541-4337.2010.00124.x.

Bátori et al.,"Ethanol and Protein from Ethanol Plant By—Products Using Edible Fungi Neurospora intermedia and Aspergillus oryzae", Hindawi Publishing Corporation, BioMed Research International, vol. 2015, Article ID 176371, 10 pages.

Berovic et al. (2003) "Submerged cultivation of Ganoderma lucidum biomass and immunostimulatory effects of fungal polysaccharides" J. Biotechnol. 103(1): 77-86.

Beuchat "Indigenous Fermented Foods", in Biotechnology Set, Second Edition (eds H .-J. Rehm and G. Reed), Wiley-VCH Verlag GmbH, Weinheim, Germany, p. 505-559, 2001.

(56) References Cited

OTHER PUBLICATIONS

Bok et al. Phytochemistry (1999) "Antitumor sterols from the mycelia of Cordyceps sinensis" 51: 891-898.
Canedo et al., "Protein enrichment of brewery spent grain from Rhizopus oligosporus by solid-state fermentation", Bioprocess Biosyst Eng (2016) 39:1105-1113.
Chang et al. (2002), "Bioactive Polysaccharides from Traditional Chinese Medicine Herbs as Anticancer Adjuvants", The Journal of Alternative and Complementary Medicine, V. 8 (5): 559-565.
Chang et al. (2009) "Gandoderma lucidum Extract Promotes Immune Responses in Normal BALB/c Mice In Vivo", in vivo, V. 23: 755-760.
ClearTaste ™ White Paper, Jan. 2016, MycoTechnology, Sustainable Neutral Taste & Aroma Non-Animal Protein, PureTaste Shiitake Protein, 5 pages.
Crafack et al., "Influencing cocoa flavour using Pichia Kluyveri and Kluyveromyces marxianus in a defined mixed starter culture for cocoa fermentation", International Journal of Food Microbiology 167: 103-116 (2013).
Moore et al., 21st Century Guidebook to Fungi by David Moore, Geoffrey D. Robson and Anthony P. J. Trinci; 17.18 The Quorn fermentation and evolution in fermenters; Updated Dec. 17, 2016, Built by David Moore with Course Genie and Dreamweaver; 8 pages.
De Melo, Rodrigues et al. (2008) Influence of Flammulina velutipes mycelia culture conditions on antimicrobial metabolite production Mycoscience 50(1): 78-8.
Denny et al.: "REVIEW Mycoprotein and health", British Nutrition Foundation Nutrition Bulletin, Jan. 1, 2008 (Jan. 1, 2008), pp. 298-310, XP55401905, Retrieved from the Internet: URL:http://onlinelibrary.wiley.com/store/10.1111/j.1467-3010.2008.00730.x/asset/j.1467-3010.2008.00730.x.pdf? v=1&t=j6xdi27x&s=4c80492be8685ba3ba396b891bf64d0a5cb2b3fd.
Dhingra et al., "Utilization of Potato Processing Waste for Compound Cattle Feed", Agricultural Engineering Today, vol. 37(4), 2013.
Diekman, "Sweeterners Facts and Fallacies: Learn the Truth about the Different Types of Sweeterners to Better Counsel Patients", Today's Dietitian 14(9): pp. 42-45, Sep. 2012.
Emden (2015) "Decaffeination 101: Four Ways to Decaffeinate Coffee" Coffee Connection; retrieved from: http://www.coffeeconfidential.org/health/decaffeination/ Jan. 29, 2015. 7 pages.
Encyclopedia Britannica, Louis Pasteur, Datasheet [online]. Copyright 2014 Encyclopedia Britannica Inc. [retrieved on Feb. 6, 2014]. Retrieved from the Internet: < URL: http://www.britannica.com/Ebchecked/topic/445964/Louis-Pasteur>. Specif, p. 3.
Finnigan et al., "Mycoprotein: A Healthy New Protein With a Low Environmental Impact", Chapter 19, Sustainable Protein Sources. DOI: http://dx.doi.org/10.1016/B978-0-12-802778-3.00019-6 ; 21 pages.
Firenzuoli et al. (2008) "The Medicinal Mushroom Agaricus blazei Murrill: Review of Literature and Pharmaco-Toxicological Problems" Evid. Based Complement Alternat. Med. 5(1): 3-15.
Han (2005) Solid-state fermentation of cornmeal with the basidiomycete Ganoderma lucidum for degrading starch and upgrading nutritional value J. Appl. Micro. 2005, 99: 910-915.
Hashim, Puziah (1997) "Effect of Processing on Flavour Precursors, Pyrazines and Flavour Quality of Malaysian Cocoa Beans". PhD thesis, Universiti Pertanian Malaysia.
He, Jianwei et al. (2010) "Patented Techniques for Detoxification of Mycotoxins in Feeds and Food Matrices" Recent Patents on Food, Nutrition & Agriculture, vol. 2:96104.
Hultberg et al., "Fungi-based treatment of brewery wastewater—biomass production and nutrient reduction", Appl Microbiol Biotechnol (2017) 101:4791-4798.
Ikrawan, Yusep (2003) Influence of Carboxypeptidases on Cocoa Specific Aroma Precursors and Methylpyrazines in Under-Fermented Cocoa Beans. PhD thesis, Universiti Putra Malaysia.
International Search Report and Written Opinion for PCT Application PCT/US2019/052236 dated Dec. 4, 2019, 18 pages.
International Preliminary Report on Patentability dated Search Report and Written Opinion for PCT Application PCT/US2018/025301 dated Sep. 2, 2018, 5 pages.
International Search Report and Written Opinion for PCT Application PCT/US2018/025301 dated Sep. 2, 2018, 9 pages.
Ishikawa et al. (2001) "Antimicrobial Cuparene-Type Sesquiterpenes, Enokipodins C and D, from a Mycelial Culture of Flammulina velutipes" J. Nat. Prod. 64(7): 932-934.
Jin et al., "A comprehensive pilot plant system for fungal biomass protein production and wastewater reclamation", Advances in Environmental Research, 2002, vol. 6, pp. 179-189.
Jin, B. et al. "Utilisation of Starch Processing Wastewater for Production of Microbial Biomass Protein and Fungal αAmylase by *Aspergillus Oryzae*", Bioresource Technology, 66:201-206 (1998). (OA.00004 Matter).
Kamimuira, Hisashi (1989) "Removal of Mycotoxins during Food Processing" Tokyo Metropolitan Research Laboratory of Public Health article: 88-94.
Kang (2003) Abstract of "Studies on chemical constituents of the mycelia from fermented culture of Flammulina velutipes" Zhongguo Zhong Yao Za Zhi 28(11): 1038-1040.
Kang (2005) Abstract of "Studies on chemical constituents in the mycelia from fermented culture of Flammulina velutipes" Zhongguo Zhong Yao Za Zhi 30(30): 193-195.
Konno et al. (2002) "Anticancer and Hypoglycemic Effects of Polysaccharides in edible and Medicinal Maitake Mushroom [*Grifola frondosa*(Dicks.: Fr.) S. F. Gray]" International Journal of Medicinal Mushrooms 4(3): 10-21.
Kühnel et al., "Aiming for the complete utilization of sugar-beet pulp: Examination of the effects of mild acid and hydrothermal pretreatment followed by enzymatic digestion", Biotechnology for Biofuels 2011, 4:14.
Kuo et al. (1996) "Cordyceps sinensis as an Immunomodulatory Agent" Am. J. Chin. Med. (1996) 24: 111-125.
Lakshmi et al. (2003) Abstract of "Antiperoxidative, antiinflammatory, and antimutagenic activities of ethanol extract of the mycelium of *Ganoderma lucidum* occurring in South India" Teratog. Carcinog. Mutagen 1: 85-97.
Lee et al. (2003) "Biological activities of the polysaccharides produced from submerged culture of the edible Basidiomycete *Grifola frondosa*" Enzyme and Microbial Technology 32(5): 574-581.
Lefeber et al., "On-farm implementation of a starter culture for improved cocoa bean fermentation and its influence on the flavour of chocolates produced thereof", Food Microbiology 30:379-392 (2012).
Liu et al. (2012) Molecules, 17:12575-12586, Improving the Fermentation Production of the Individual Key Triterpene Ganoderic Acid Me by the Medicinal Fungus Ganoderma lucidum in Submerged Culture.
MicrobiologyBytes. Introduction to Mycology. Datasheet [online'. Updated Apr. 8, 2009 [retrieved on Feb. 6, 2014]. Retrieved from the Internet: <URL: http://www.microbiologybytes.com/introduction/myc1.html>. Specif, p. 8.
Miri et al. "Flow induced fibre alignment in Mycoprotein paste", Food Research International, Elsevier, Amsterdam, NL, vol. 38,No. 10, Dec. 1, 2005 (Dec. 1, 2005), pp. 1151-1160, XP027868270, ISSN: 0963-9969 [retrieved on Dec. 1, 2005].
Mitra et al.: "Value-added oil and animal feed production from corn-ethanol stillage using the oleaginous fungus Mucor circinelloides", Bioresource Technology, Elsevier, Amsterdam, NL, vol. 107, Mar. 1, 2012 (Mar. 1, 2012), pp. 368-375, XP002696572, ISSN: 0960-8524, DOI: 10.1016/J.BIORTECH.2011.12.031 [retrieved on Dec. 14, 2011.
Ali, Mohamed, Aisha Bibi (2010) Production of pyrazine flavours by mycelial fungi. Master's thesis, University of Pretoria.
Moo-Young et al.: "Fermentation of cellulosic materials to mycoprotein foods", Biotechnology Advances, Elsevier Publishing, Barking, GB, vol. 11, No. 3, Jan. 1, 1993 (Jan. 1, 1993), pp. 469-479 XP025222949, ISSN: 0734-9750, DOI: 10.1016/0734-9750(93)90015-F [retrieved on Jan. 1, 1993.

(56) References Cited

OTHER PUBLICATIONS

Morris et al. (2003) Abstract of "Immunomodulating Effects of Hot-Water Extract From *Pleurotus ostreatus* Mycelium on Cyclophosphamide Treated Mice" Micologia Aplicada Internacional 15(1): 7-13.

Nair et al. "Mycelial Pellet Formation by Edible Ascomycete Filamentous Fungi, *Neurospora Intermdeia*", AMB Express. 6:31, 10 pages (2016) (.00004 Office Action).

Nitayavardhana et al., "Production of protein-rich fungal biomass in an airlift bioreactor using vinasse as substrate", Bioresource Technology, vol. 133 (2013) 301-306.

Nowrousian et al. "The novel ER membrane protein PRO41 is essential for sexual development in the filamentous fungus Sordaria macrospora" Molecular microbiology 64(4): 923-937, 200.

Ogundero, "Thermophilic fungi and fermenting cocao beans in Nigeria", Mycopathologia 82, 159-165 (1983).

Pandy et al. (2000) "Use of Various Coffee Industry Residues for the Cultivation of Pleurotus streatus in Solid State Fermentation", Acta Biotechnol. V 20(1):41-52.

Paterson (2006) "Ganoderma—A therapeutic fungal biofactory" Phytochemistry 67:1985-2001.

Rasmussen et al., "Water reclamation and value-added animal feed from corn-ethanol stillage by fungal processing", Bioresource Technology 151 (2014) 284-290.

Rodger: "Production and Properties of Mycoprotein as a Meat Alternative", Food Technology, Institute of Food Technologists, Chicago, IL, US, vol. 55,No. 7, Jul. 1, 2001 (Jul. 1, 2001), p. 36, XP001101831, ISSN: 0015-6639.

Russell, R. et al. 2006. Ganoderma—a therapeutic fungal biofactory. Phytochemistry 67:1985-2001. specif, pp. 1985, 1987-1988, 1994-1995, 1997-1998.

Samir Kumar Khanal, Utilization of Local Agri-processing By-products to Produce Fungal Protein for Aquatic Feed Production, Local Feed Workshop, Oceanic Institute of Hawaii Pacific University, Nov. 21, 2014, Honolulu 26 pages.

Sankaran et al., "Use of Filamentous Fungi for Wastewater Treatment and Production of High Value Fungal Byproducts: A Review", Critical Reviews in Environmental Science and Technology, 40:400-449, 2010.

Saoharit Nitayavardhana et al.: "Production of protein-rich fungal biomass in an airlift bioreactor using vinasse as substrate", Bioresource Technology, vol. 133, Jan. 30, 2013 (Jan. 30, 2013), pp. 301-306, XP55645529, Amsterdam, NL ISSN: 0960-8524, DOI: 10.1016/j.biortech.2013.01.073.

Schtigerlet al., "Investigation of the use of agricultural byproducts for fungal protein production", Process Biochemistly, vol. 32, No. 8, pp. 705-714, 1997.

Schwan, "Cocoa Fermentations Conducted with a Defined Microbial Cocktail Inoculum", Applied and Environmental Microbiology, vol. 64, No. 4, Apr. 1998.

Schwan, "The Microbiology of Cocoa Fermentation and its Role in Chocolate Quality", Critical Reviews in Food Science and Nutrition, 44:205-221 (2004).

Shao et al. (2001) "Determination of nucleosides in natural Cordyceps sinensis and cultured Cordyceps mycelia by capillary electrophoresis" Electrophoresis 22(1): 144150.

Sone et al. (1985) "Structures and Antitumor Activities of the Polysaccharides Isolated from Fruiting Body and the Growing Culture of Mycelium of Ganoderma lucidum", Agric. Biol. Chem., V. 49(9): 2641-2653.

Souza et al.: "Edible Protein Production by Filamentous Fungi using Starch Plant Wastewater", Waste and Biomass Valorization, Springer Netherlands, NL, vol. 10, No. 9,Mar. 7, 2018 (Mar. 7, 2018), pp. 2487-2496, XP036859959, ISSN:1877-2641,DOI: 10.1007/S12649-018-0265-2 [retrieved on Mar. 7, 2018].

Souza Filho et al., "Production of Edible Fungi from Potato Protein Liquor (PPL) in Airlift Bioreactor", Fermentation 2017, 3, 12; doi:10.3390/fermentation3010012; 12 pages.

Sparringa et al.: "Glucosamine content of tempe mould, Rhizopus oligosporus", International Journal of Food Microbiology, vol. 47, No. 1-2, Mar. 1, 1999 (Mar. 1, 1999), pp. 153-157, XP55645542,NL ISSN: 0168-1605, DOI: 10.1016/S0168-1605(99)00020-3.

Stamets (2003) Chapter 12, pp. 89-92 Culturing Mushroom Mycelium on Agar Media.

Stevens et al., "Production of Microbial Biomass Protein from Potato Processing Wastes by Cephalosporium eichhorniae", Applied And Environmental Microbiology, vol. 53, No. 2, Feb. 1987, pp. 284-291.

Tang et al., "Current progress on truffle submerged fermentation: a promising alternative to its fruiting bodies", Appl Microbiol Biotechnol (2015) 99:2041-2053.

Taylor, J. (2001) "Measuring Fungal Growth." Chapter 3.8 In: Microorganisms and Biotechnology, 2nd ed., Thomas Nelson, Ltd. 2001 Delta Place, Cheltenham, U. K. (ISBN 0 17 448255 8). Specif. p. 4 (book p. 44).

Trinci: "'Quorn' mycoprotein", MYCOLOGIST, vol. 5, No. 3, Jul. 1, 1991 (Jul. 1, 1991), pp. 106-109, XP55638561, GB ISSN: 0269-915X, DOI:10.1016/S0269-915X(09)80296-6.

Tsubouchi et al. (1987) "Effect of roasting on ochratoxin A level in green coffee beans inoculated with Aspergillus ochraceus", Mycopathologia 97: 111-115.

Ulziijargal et al. (2011) : Nutrient Compositions of Culinary-Medicinal Mushroom Fruiting Bodies and Mycelia Int. J. Med. Mushrooms 13(4): 343-349.

Van Leeuwen et al., "Fungal Treatment of Crop Processing Wastewaters with Value-Added Co-Products", Green Energy and Technology, DOI: 10.1007/978-1-4471-2324-8_2, Springer-Verlag London Limited 2012. 33 pages.

Wasser (2002) "Medicinal mushrooms as a source of antitumor and immunomodulating polysaccharides" Appl Microbiol Biotechnol 60: 258-274.

Willis, W.L. et al. (2010) Effect of Dietary Fungus Myceliated Grain on Broiler Performance and Enteric Colonization with Bifidobacteria and *Salmonella International Journal of Poultry Science.*, 9(1): 48-52.

Wu et al. (2011) "Ling Zhi-8 mediates p53-dependent growth arrest of lung cancer cells proliferation via the ribosomal protein S7-MDM2-p53 pathway" Carcinogenesis 32(12): 1890-1896.

Xiros et al., "Hydrolysis and fermentation of brewer's spent grain by Neurospora crassa", Bioresource Technology 99 (2008) 5427-5435.

Yin et al. (2010) "Purification, Characterization and Immuno—Modulating Properties of Polysaccharides Isolated from Flammulina velutipes Mycelium" Am. J. Chin. Med. 38(1): 191-204.

Zhang et al. (2004) Life Sciences, 75:2911-2919, Induction of HL-60 apoptosis by ethyl acetate of Cordyceps sinensis fungal mycelium.

Zhang et al. (2010) "Mycelial growth and polysaccharide content of *Polyporus umbellatus*" Journal of Medicinal Plants Research 4(18): 1847-1852.

Zhong et al. (2004) "Submerged Cultivation of Medicinal Mushrooms for Production of Valuable Bioactive Metabolites", Adv Biochem Engin/Biotechnol V. 87: 25-59.

Zhou et al. (2009) "Cordyceps fungi: natural products, pharmacological functions and developmental products" Journal of Pharmacy and Pharmacology 61:279-291.

Pu et al., "Preparation and Application of a Novel Bioflocculant by Two Strains of *Rhizopus* sp. Using Potato Starch Wastewater as Nutrilite", Bioresource Technology, Jun. 2014, vol. 162, pp. 184-191.

Krull, R., et al., "Characterization and Control of Fungal Morphology for Improved Production Performance in Biotechnology", J. Biotechnol., Jan. 20, 2013, vol. 163(2), pp. 112-123.

Cairns, et al., "Moulding the mould: understanding and reprogramming filamentous fungal growth and morphogenesis for next generation cell factories," Biotechnology for Biofuels, vol. 12, 77, 18 pages (2019).

Foster, "Here's How (and Why) to Slice Meat Against the Grain," Kitchn, retrieved Aug. 19, 2021 from https://www.thekitchn.com/heres-exactly-how-to-slice-meat-against-the-grain-and-why-you-should-be-doing-it-meat-basics-215798, 5 pages (2015).

(56) References Cited

OTHER PUBLICATIONS

Markham, et al., "Choline: Its role in the growth of filamentous fungi and the regulation of mycelial morphology," FEMS Microbiology Reviews, vol. 10(3-4), pp. 287-300 (1993).
Veiter, et al., "The filamentous fungal pellet-relationship between morphology and productivity," Applied Microbiology and Biotechnology, vol. 102, pp. 2997-3006 (2018).
Walisko, et al., "The Taming of the Shrew-Controlling the Morphology of Filamentous Eukaryotic and Prokaryotic Microorganisms," Adv. Biochem. Eng. Biotechnol., pp. 1-27 (2015).
Wiebe, et al., "Effect of Choline on the Morphology, Growth and Phospholipid Composition of Fusarium graminearum," Journal of General Microbiology, vol. 135(8), pp. 2155-2162 (1989).
Bobby B., "How to Cut Salmon Sashimi and Nigiri," Blade Advisor, retrieved Aug. 19, 2021 from https://bladeadvisor.com/how-to-cut-salmon-sashimi-and-nigiri/, 10 pages (2019).
Wikipedia, "Mycelium", retrieved Aug. 19, 2021 from <https://en.wikipedia.org/w/index.php?title=Mycelium&oldid=761708709>, Jan. 24, 2017, 3 pages.
Wikipedia, "Protein Digestibility Corrected Amino Acid Score", retrieved Aug. 19, 2021 from <https://en.wikipedia.org/w/index.php?title=Protein_Digestibility_Corrected_Amino_Acid%20Score&oldid+809488538>, Nov. 9, 2017, 4 pages.
Gmoser et al., "Pigment Production by the Edible Filamentous Fungus Neurospora Intermedia" 4(11):1-15 (Feb. 2018).
U.S. Appl. No. 18/496,682.
Sastraatmadja, D. D. et al."Production of High-Quality Oncom, a Traditional Indonesian Fermented Food, by the Inoculation with Selected Mold Strains in the Form of Pure Culture and Solid Inoculum," J. Grad. Sch. Agr. Hokkaido Univ., vol. 70, Pt. 2: pp. 111-127 (2002).
Ho, C.C. "Identity and Characteristics of Neurospora intermedia Responsible for Oncom Fermentation in Indonesia", Food Microbiology, vol. 3, pp. 115-132 (1986).
Huggins, T. M. et al., "Controlled Growth of Nanostructured Biotemplates with Cobalt and Nitrogen Codoping as a Binderless Lithium-Ion Battery Anode", ACS Applied Materials & Interfaces, vol. 8, p. 26868-26877 (2016).
Dekkers, B. L. et al. "Structuring Processes for Meat Analogues," Trends Food Sci. & Technol., vol. 81, p. 2536 (Nov. 2018).
Hoffman, J.R., et al. "Protein—Which is Best?" J. Sports Sci. and Med., vol. 3, p. 118-130 (2004).
Tu, Chuanhai et al., "Characterization of Fermented Okara Powder and its Effects on lipid Oxidation of Emulsion-type Sausage Pork Sausage During Cold Storage", https://doi.org/10.7287/peerj.preprints.2636v1, published online Dec. 13, 2016.
Tu, Zongcai et al. "Study on Production of High-Activity Dietary Fiber from Soybean Dregs in Neurospora crassa", Food and Fermentation Industries, vol. 34(4), p. 68-70 (2008). (English Abstract).
Ren, Zhi-Qing et al. "Study on fermented by Neurospora crassa to improve structural style of soybean meal nutrition", Science and Technology of Food Industry, vol. 37(12), pp. 222-249 (2016). (English Abstract).
Liu, P. et al."Bio-transformation of agri-food wastes by newly isolated Neurospora crassa and Lactobacillus plantarum for egg production", Poultry Science, vol. 95, pp. 684-693 (2016).
Zhou, R. et al. "Fermented Soybean Dregs by Neurospora crassa: a Traditional Prebiotic Food", App. Biochem. Biotech., vol. 189, pp. 608-625 (published online May 11, 2019).
Kanti, A. et al. "Comparison of Neurospora crassa and Neurospora sitophilia for phytase production at various fermentation temperatures", Biodiversitas, vol. 17(2), p. 769-775 (Oct. 2016).
Asri, R. et al. "Use of Mushrooms Neurospora Crassa in Making Steam Rangen for Improving Nutrition and Community Welfare", Pelita, vol. IV(1), p. 1-12 (2009) (Foreign language document with Google machine translation).
Jiang et al., "UV Induced Conversion During Drying of Ergosterol to Vitamin D In Various Mushrooms: Effect of Different Drying Conditions," Trends in Food Science & Technology, pp. 200-210 (2020).

Wu et al., "Statistical Optimization of Ultraviolet Irradiate Conditions for Vitamin D2 Synthesis In Oyster Mushrooms (Pleurotus Ostreatus) Using Response Surface Methodology," PLoS One, 9(4): e95359; pp. 1-7 (2014).
Pape et al., "FDA GRAS Notice GRN No. 91"; Nov. 2001:74 pages.
Kumitch, HM, et al., "Effect of fermentation time on the physicochemical and functional properties of pea protein-enriched flour fermented by Aspergillus oryzae and Aspergillus niger," Cereal Chem.; 97: 416-428 (2020). https://doi.org/10.1002/cche.10257.
Souza Filho, "Fungi-based biorefinery model for food industry waste: progress toward a circular economy," University of Boras, pp. 1-88 (2018). ORCID iD: 0000-0002-1711-7294.
Zahler, J., "Improving the Nutritional Characteristics of Plant Feedstuff ByProducts Using Fungal Metabolism," Electronic Theses and Dissertations. 2689; pp. 1-134 (2018). https://openprairie.sdstate.edu/etd/2689.
U.S. Appl. No. 18/364,750, filed Aug. 3, 2023.
U.S. Appl. No. 18/496,682, filed Oct. 27, 2023.
Moo-Young, M. et al., "Fermentation of Cellulosic Materials to Mycoprotein Foods," Biotech. Adv., vol. 11, pp. 469-479 (1993).
Ferreira, J. A. et al., "Production of ethanol and biomass from thin stillage by Neurospora intermedia: A pilot study for process diversification," Eng. Life Sci., vol. 15, pp. 751-759 (2015).
Wei, Y., "Study on the effects of Neurospora robusta fermentation on the nutritional components of bean dregs and the isolation and purification of polysaccharides", Zhangqiao Research, Nanchang University, vol. 214, p. 1 (2007). (English Abstract).
Lin, B.-S et al., "Isolation, identification, genome variation and functional analysis of a strain form Neurospora crassa", Microbiology China, vol. 47(3), p. 771-781 (2020).
Yassin, M.S.B.M., "The physiological and ecological characteristics of the red bread mould", Ph.D. Thesis, University of Bath, ProQuest, pp. 1-201 (1980).
Rizal, Y. et al. "Comparisons of nutrient contents and nutritional values of palm kernel cake fermented by using different fungi", Pakistan Journal of Nutrition, vol. 12(10), pp. 943-948 (2013).
Zahler, J., "Improving the Nutritional Characteristics of Plant Feedstuff By-Products Using Fungal Metabolism", Electronic Theses and Dissertations. 2689, South Dakota State University, pp. 1-146 (2018).
Zapata, A. et al., "Testing the potential of using the fungus Neurospora crassa to convert human waste into edible protein", Valparaiso University, ValpoScholar, pp. 1-2 (2011). (English Abstract).
Jun, Y. et al., "Study on the Change of Nutrition Components in Neurospora. Crassa Fermentation Process of Soybean Residue", Journal of Chinese Institute of Food Science and Technology, vol. 13(12), pp. 1-5 (2013). (English Abstract).
Yang Feng-ling et al., "Progress in the Production of Carotenoids from Neurospora crassa", Food and Fermentation Industries, State Key Laboratory of Food Science and Technology , Nanchang University, vol. 38(11), p. 115-119 (2012). (Engllish Abstract).
"Indonesian Soybean Product 4: Oncom", Foodiepelago Your Resource of Indonesian Food, https://foodiepelago.wordpress.com/2013/09/28/indonesian-soybean-product-4-oncom/, pp. 1-5 (2013).
Macris, B.J. et al., "Solid State Fermentation of Straw with Neurospora Crassa for CMCase and Beta-Glucosidase Production", Biotechnology Letters, vol. 9(9), pp. 661-664 (1987).
Dwidjoseputro, D., "Studies on Monilia sitophila from Indonesia", bulletin of the Torrey Botanical Club , vol. 88(6), pp. 404-411 (Nov.-Dec. 1961).
Bartholomai, B. M. et al., "Safety evaluation of Neurospora crassa mycoprotein for use as a novel meat alternative and enhancer", Food and Chemical Toxicology, vol. 168, p. 113342, 1-14, (2022).
Neurospora crassa Shear et Dodge 24914, https://www.atcc.org/products/24914, Product citation, pp. 1-4 (downloaded Feb. 29, 2024).
Tamang, J. P., et al., "Review: Diversity of Microorganisms in Global Fermented Food and Beverages", Frontiers in Microbiology, Article 377, pp. 1-28 (2016).
Tamang, J. P. et al., "Chapter 1: Microorganisms in Fermented Foods and Beverages", pp. 1-110 (2015).
Hui, Y. H. et al., "Handbook of Plant-Based Fermented Food and Beverage Technology", Second Edition, 319 pages (2012).

(56) References Cited

OTHER PUBLICATIONS

Surono, I. S., "Ethnic Fermented Food and Beverages of Indonesia", Ethnic Fermented Foods and Alcoholic Beverages of Asia, pp. 341-382 (2016).
Steinkraus, K., "Handbook of Indigenous Fermented Foods", Second Edition, pp. 1-110 (1996).
Santoso, U. et al., "Effect of Fermented Sauropus androgynus Leaves on Meat Composition, Amino Acid and Fatty Acid Compositions in Broiler Chickens", Pakistan Journal of Nutrition, vol. 14(11), pp. 799-807 (2015).
Qiu, Y. et al., "Analysis of key fungi and their effect on the edible quality of HongJun tofu, a Chinese fermented okara food", LWT—Food Science and Technology, vol. 172, pp. 1-12, 114151 720 (2022).
Gmoser, R., "Circular bioeconomy through valorisation of Agro-industrial residues by the edible filamentous fungus Neurospora intermedia", University of Boras, pp. 1-212 (2021).
Qiu, Y., "Fermentation with a Multi-Strain to Enhance the Flavor of Hongjun Tofu, a Chinese Fermented Okara Food", LWT—Food Science and Technology, vol. 189, pp. 1-12 (2023).
"Oncom, Encyclopedia, Science News & Research Reviews", pp. 1-9, Wikipedia article -no. date. Effective date Apr. 24, 2024.
Surya, R. et al., "Antioxidant profile of red oncom, an Indonesian traditional fermented soyfood", Food Research, vol. 7 (4), pp. 204-210 (2023).
Yao, H. et al., "Differential analysis and bioactivity identification of Neurospora crassa metabolites based on okara by widely-targeted metabolomics", LWT—Food Science and Technology, vol. 174, pp. 1-8, 114441 (2023).
Nuraini, N., "Improving the Quality of Tapioca by Product Through Fermentation by Neurospora crassa to Produce B Carotene Rich Feed", Pakistan Journal of Nutrition, vol. 8(4), pp. 487-490 (2009).
"Notice on approving and publishing the second batch of municipal intangible cultural heritage list of Meizhou City", Office of Meizhou Municipal People's Government, Mei City Government No. 19, pp. 1-3 (2009).
Lubick, N., "Multitalented Mold Sequenced Neurospora crassa's DNA may yield a broad range of insights", Biology, https://www.science.org/content/article/multitalented-mold-sequenced, pp. 1-2 (2003).

Burton, E. G. et al., "Regulation of methionine biosynthesis in Neurospora crassa", Archives of Biochemistry and Biophysics, vol. 168(1), pp. 219-229 (1975). (Abstract).
Sanders, D. et al., "Control of Intracellular pH. Predominant Role of Oxidative Metabolism, Not Proton Transport, in the Eukaryotic Microorganism Neurospora", J. Gen. Physiol., vol. 80, pp. 377-402 (1982).
Wiebers, J. L. et al. "Interrelationships of Sulfur Amino Acids in The Pool and Cellular Protein Of Neurospora crassa.", Biochmica Et Biophysica Acta., vol. 117(2), pp. 403-409 (1966). (Abstract).
Finnigan, T. et al., "Chapter 19—Mycoprotein: A Healthy New Protein with a Low Environmental Impact.", Sustainable Protein Sources., pp. 305-325 (2017). (Abstract).
Miller, SA et al., Evaluating the Safety and Nutritional Value of Mycoprotein.: , Food Technology, vol. 55(7), pp. 42-47 (2001). (Abstract).
Espin, G. et al., "Effect of the Deprivation of Amino Acids on Conidia of Neurospora crassa," Journal of General Microbiology, vol. 104, pp. 233-240 (1978).
Krull, R. et al., "Filaments in Bioprocesses," Advances in Biochemical Engineering/Biotechnology, vol. 149, 317 pages (2015).
Knight, N. et al., "The thermal stability of Quorn (TM) pieces," International Journal of Food Science and Technology, vol. 36, pp. 47-52 (2001).
Wucherpfennig, T. et al., "Chapter 4. Morphology and Rheology in Filamentous Cultivations," Advances in Applied Microbiology, vol. 72, pp. 89-136 (2010).
Wei, Y., "Study on the effects of Neurospora robusta fermentation on the nutritional components of bean dregs and the isolation and purification of polysaccharides," Masters Thesis, Zhangqiao Research, 3 pages (2007). (Abstract).
Huggins, M.T., "Synthesis of Biomass Derived Carbon Materials for Environmental Engineering and Energy Storage Applications," Ph.D. Thesis to the University of Colorado, Department of Civil, Environmental, and Architectural Engineering, 159 pages (2016).
Souza Filho, P.F. et al., "Vegan-mycoprotein concentrate from pea-processing industry byproduct using edible filamentous fungi," Fungal Biology and Biotechnology, vol. 5, No. 5, 10 pages (2018).

\* cited by examiner

ENHANCED AEROBIC FERMENTATION METHODS FOR PRODUCING EDIBLE FUNGAL MYCELIUM BLENDED MEATS AND MEAT ANALOGUE COMPOSITIONS

CROSS REFERENCE TO RELATED APPLICATIONS

The present application is a continuation of U.S. patent application Ser. No. 16/586,150, filed Sep. 27, 2019, now U.S. Pat. No. 11,470,871, which is a continuation of U.S. patent application Ser. No. 16/578,099, filed Sep. 20, 2019, now U.S. Pat. No. 11,058,137, which claims the benefit of U.S. provisional application Ser. No. 62/733,925, filed Sep. 20, 2018, which applications are hereby incorporated by reference in their entirety.

FIELD OF THE INVENTION

Provided herein are shelf-stable protein food ingredients, food products comprising the shelf-stable protein food ingredients, methods of their production, and methods of their use.

BACKGROUND

To keep up with global population growth projected to reach 10 billion by 2050, we must be able to produce 70% more food on Earth. The average American consumes over 200 pounds of meat per year. Meat as a protein source is becoming increasingly costly to humanity due to associated habitat conversion, water, and resource use. As environmental resources become more scarce, we cannot afford to invest valuable nutrient resources into inefficient food production processes such as farming of animals. The tasks of reducing meat consumption along with creating sustainable alternatives will be required to meet the protein demand of the future. On average, 5% of the calories from animal feed make it into the meat consumed by humans. These vital nutrients are only becoming more precious a commodity. The environmental budget of the planet will not allow humans to continue under such tremendous inefficiency.

Technical Problem

The alternative protein industry is booming. The current landscape of plant protein ingredients is incredibly limited. Almost every product on the market relies on either wheat, soy, or pea proteins. There are two realms of texturization that companies use to produce their meat analogues—wet texturization and dry texturization. Virtually all texturized plant protein sold today as an ingredient is as a dry texturized protein. These ingredients are limited to the versatility of twin-screw extrusion systems, and the functionality of the three aforementioned plant protein inputs. The ingredients being produced are very similar to each other, and the two most widely used proteins (wheat and soy) are both in the list of the eight most common allergens. Texturized pea protein is still very expensive. In order to move the industry forward, we need alternative ingredients for the plant-based protein world.

Cutting the amount of animal-derived meat needed to produce a meat product is a concept being investigated by many key players in the meat industry. Certain ingredients in existing blended meats lack the protein, texture, and filamentous nature of muscle and fat in meat. These ingredients, described as meat extenders, typically only consist of single ingredient, e.g. flours, powders, or crumbs, lacking nutrition and enhancement of the meat.

The food and beverage industries produce high volume food grade waste streams containing quality starches, sugars, nitrogen, fats, vitamins, minerals, and other nutrients. This material often goes to feed animals at an inefficient conversion rate or is treated as a complete waste and sent to landfills or treatment facilities. Leftover material from processing, extraction, and cultivation are available on a consistent basis. These are valuable food grade nutrients that we cannot afford to lose.

Commercial plant agriculture is dependent on environmental parameters beyond the control of man. Weather, climate, wind, pathogens, blight, disasters, and more can unpredictably wipe out entire areas of food production. Controlled agriculture is essential; however, it is limited to indoor plant farming reliant on artificial lighting powered primarily by the electric grid and in effect, coal and natural gas.

Significant resources are being directed towards sustainable methods of producing cultured meats and meat analogues. Meat alternatives in the marketplace are mostly derived from plant biomass. Plant based analogues and meat fillers commonly require significant manipulation and additives to mimic the texture, nutritional profile, and properties of meat.

Current meat analogues rely almost entirely on texturized vegetable proteins (TVP). These ingredient supplies are reliant on costly texturization processes, limited manufacturing capacity, environmental impacts on cultivation, supply of raw material, and often times processing aids. These ingredients have functional limitations as they can only achieve certain textures and qualities. The base plant biomass of most TVP is wheat and soy, two of the eight common allergens and therefore not preferred as ingredients. Some texturized pea exists in the marketplace, however, it is limited in use by its high cost and constricted supply.

Solution

Provided herein are shelf-stable protein food ingredients that are versatile in production methods, functionality, and form. The ingredients can be completely allergen free and potentially cheaper than texturized pea protein. The shelf-stable protein food ingredients can have substantial impacts in the types of alternative protein food ingredients and products in the marketplace.

In one aspect, provided herein are fermented shelf-stable protein food ingredients that can be dry, stored, and readily integrated into the food ingredient supply chain. These ingredients are designed to be meat-like, versatile, and cost-effective to produce. They can be readily substituted for plant based protein ingredients and can be produced for a lower cost in many embodiments.

In one aspect, provided herein are fermentation processes that harness waste nutrient streams from crop and food processing. Harnessing these streams has a multitude of benefits for society, and our planet as a whole. By utilizing these nutrient streams and converting them into high quality food ingredients and products, we are garnering a quality protein source without requiring significant land and carbon impacts on the planet compared to meat or even plants.

Fungi are decomposers. They complete degradation of complex organic molecules like lignin and cellulose in nature. By excreting digestive enzymes and acids, fungi are able to convert more complex carbohydrates into simple fermentable sugars. Their incredible efficiency at decomposing and consuming low value waste streams can be utilized to produce high value, quality food for the masses with low-cost, inexpensive inputs.

In one aspect, provided herein are shelf-stable protein food ingredients that create a means of reducing and replacing animal meat products. These shelf-stable protein food ingredients can provide all essential amino acids (significant amounts of protein), fiber, quality fats, and most essential micronutrients and vitamins. In certain embodiments, the production process is efficient and environmentally sustainable. In another aspect, processes for producing these foods are disclosed herein.

The shelf-stable protein food ingredients described herein can be produced in a refined, controlled, environment that mitigates most of the problems associated with traditional agriculture. The shelf-stable protein food ingredients can comprise fungi cultivated in optimized fermentation systems with low physical, financial, and environmental footprints. These systems are more typically utilized in the production of penicillin, enzymes, and acids but can be adapted for use in the production of food ingredients.

Filamentous fungal mycelium has been consumed for centuries in the forms of tempeh, oncom, koji, and other foods, some of which are mentioned below. These products consist of filamentous fungi grown on solid substrates. Soy, rice, and other solid substrates are nutritious; however, these solid substrates remain in the end product and dilute the potential end protein/nutrient content. These ingredients also hold dietary value on their own and do not require the fungi to become valuable to the human diet. They may be enhanced by the fungi; however, the fungal cells play a minor role in the end product.

In certain embodiments, the food ingredients and food products provided herein comprise fungal species established in human consumption and have stood the test of time. *Aspergillus oryzae* is the species used to make Koji (a fermented rice used in the production of sake, miso, and soy sauce). *Rhizopus oryzae* is a species used in fermenting tempeh. *Cordyceps militaris* and *Cordyceps sinensis* are edible fungi used in traditional Chinese Medicine. *Tuber magnatum*, better known as the Black Truffle, is an edible fungus known for its array of aromatic compounds that are responsible for its sought after flavor. *Fusarium* has been utilized as a protein source. *Penicillium* is used in cheese making. *Neurospora intermedia* and *Neurospora sitophila* are used to ferment oncom (a fermented tempeh-like soy, peanut, or legume food very commonly consumed on the mainland of Indonesia (Java) for centuries).

Filamentous fungi are known for their rapid cell replication, aggressive digestion, colonization timing, adaptability, and ease of propagation. This makes them well suited for scaled food production.

Food Ingredients

Filamentous fungal mycelium maintains a texture similar to ground meat with minimal manipulation. Filamentous fungi mycelium described herein comprises groups of connected cells fused end to end in filaments called hyphae. These hyphae typically range from 2-16 microns in diameter and can be centimeters long. These hyphae are typically one single cell thick. These morphologies give the hyphae naturally occurring texture properties similar to muscle fiber as a result of the bundling of the hyphae and the substantial moisture retention capacity of the mycelium. This makes mycelium a perfect candidate for food ingredients and food products.

In certain embodiments, the fungal mycelium is processed into a shelf-stable protein food ingredient that can be hydrated and used on its own or, advantageously, in a variety of food products including but not limited to meat extenders, meat analogues, cultured meat cell scaffoldings, and other food products requiring textured proteins. As used herein, these "textured cultured proteins" (hereinafter "TCP") are dry, shelf stable, and easily used as a replacement for lower quality more expensive texturized vegetable proteins (hereinafter "TVP").

In certain embodiments, filamentous fungal mycelium described herein comprises significant concentrations of nutrients. In certain embodiments, crude protein accounts for up to 60% of the untreated desiccated biomass. Most species contain all of the essential amino acids of the human diet. Many species contain all of the necessary B vitamins when un-supplemented (except B12). The mycelium contains many dietary minerals needed in the human diet including but not limited to zinc, iron, manganese, magnesium, potassium, selenium and calcium. All of these minerals except for zinc have been shown to be more bioavailable to the body when sourced from mushrooms and fungi compared to meat and plant sources. The mycelium is naturally high in fiber.

In certain embodiments, the fat composition of the mycelium described herein comprises or consists of mostly mono- and polyunsaturated fats and is very low in saturated fats. The biomass also may contain omega-6, linoleic acid, and omega-3, linolenic acid.

In certain embodiments, the dry shelf-stable ingredients described herein comprise significant fiber. This substantial concentration of dietary fiber in the TCP is beneficial when consuming TCP as a meat alternative, as well as being beneficial in meat/TCP blends. The present fiber increases the digestibility and bioavailability of the nutrients in the meats consumed in the blend.

It is therefore an aspect described herein to produce a food ingredient using fungi, many species of which are already accepted in their recognition of safety in the diet of humans and significantly higher in protein and fungal cells than classic fermented foods that contain some of these species.

Phosphates are commonly used in meat products to increase moisture retention by creating space between proteins. Provided herein are filamentous mycelium that can retain over 80% water. At levels of 60-85% water content the dry shelf-stable ingredient of the present invention mixes well with meats and acts as a tackifying agent helping to bind the meat while holding moisture in the meat mixture. The filamentous nature of the mycelium maintains natural space between proteins. This moisture helps the meat retain its volatile aromatics effectively preventing flavor loss. This may have implications is shelf life extension of some meat products. Upon dehydration, the mycelium described herein can remain shelf stable and retain a similar water content to the fresh material when re-hydrated.

Process

By using fermentation to produce these high protein textured ingredients, carbohydrates, other nutrients, and oxygen are converted into protein. Such methods can use less space, resources, and time than those of conventional conversions in animal agriculture.

Filamentous fungi fermentation can be carried out with waste streams as primary sources of nutrients, displacing the need to introduce so many purified nutrients into the growing medium.

Beet pulp, potato peel and processing water, processed grains, process fruits, rice polishings, and much more are abundant and available and can be used for sourcing of components in fungal fermentation substrate. Filamentous fungi effectively convert sugars and starches from these sources into biomass at a high efficiency. Some industrial fermentation operations, such as Cargill's lactic acid plant in Blair, Nebraska, USA, employ these concepts. Cargill uses beet pulp from refining sugar at the Blair plant for their primary carbohydrate source for the production of lactic acid.

In some embodiments more traditional fermentation substrates are used for producing the TCP described herein.

Food Products

Converting diet to meat alternatives has a place in the changing diet of humans; however, meat consumption is unlikely to be entirely replaced. The concept of extended meats has existed in the art for years. By simply extending the meat in processed meat products, one can significantly reduce overall meat production and demand. Current extension agents provide only some of the needed properties to have an indistinguishable profile in the blended meat. Mushrooms like portabellas are sometimes used to dilute meat and retain moisture, but only provide some of the desired properties of meat extenders while lacking others.

In certain embodiments the food ingredients described herein provide an alternative to texturized vegetable protein (TVP), the core ingredient in most meat analogues on the market.

It is therefore an aspect described herein to utilize the food ingredients provided herein for applications including but not limited to meat extension products, meat analogue products, baked good products, food products requiring binding agents, food products requiring gels, food products needing protein, food products needing fiber, and other food products.

SUMMARY

In one aspect, provided herein are shelf-stable protein food ingredients. The shelf-stable protein food ingredients comprise cultured fungal biomass and a limited amount of water. The fungal biomass and other ingredients are described in detail herein. The shelf-stable food ingredients comprise particles of sizes and forms with properties described herein. Advantageously, the shelf-stable protein food ingredients can be stored, transported, and delivered within the food supply. They can be sold or consumed as is, or, preferably, they can be combined with other food ingredients to provide food ingredient compositions and food products.

In another aspect, provided herein are food products. The food products comprise one or more of the shelf-stable protein food ingredients and one or more additional food ingredients. The additional food ingredients can be meat proteins, plant proteins, combinations thereof, or any additional food ingredient deemed useful by the practitioner of skill in the art. The food products can be consumed by animals, for instance mammals. In certain embodiments, the food products are for pet consumption. In certain embodiments, the food products are for human consumption.

In another aspect, provided herein are methods for producing the shelf-stable protein food ingredients. In certain embodiments, the methods comprise the steps of culturing fungal biomass in a growth medium, harvesting the fungal biomass, optionally processing the fungal biomass, optionally sizing the fungal biomass to form particles, and drying the particles to form the food ingredients.

In certain embodiments, provided herein are methods of producing a meat-textured high protein ingredient from filamentous fungal mycelium produced with plant biomass hydrolysate as the primary growth media. The methods comprise the steps of generating plant biomass hydrolysate/extract; enhancing the hydrolysate with supplements to enhance yields, nutritional profile, and morphology; sterilizing said substrate; inoculating substrate with filamentous fungi; propagating the filamentous fungus in optimized aerobic fermentation conditions; harvesting pure fungal mycelium, de-watering, shaping, sizing, drying and pasteurizing; integrating dried and shaped ingredient into blended meat extension ingredients; hydrating and blending hydrated ingredient in ground meats; and utilizing aforementioned ingredients in blended plant and mushroom products.

In certain embodiments, provided herein are methods of producing a shelf-stable protein ingredient from filamentous fungal mycelium with substrates based on glucose, sucrose, sugars, starches, and/or biotin as well as salt forms of nitrogen, phosphorous, potassium and other necessary elements. The methods comprise mixing said substrate; sterilizing said substrate; inoculating substrate with filamentous fungi; propagating the filamentous fungi in optimized aerobic fermentation conditions; harvesting pure fungal mycelium, de-watering, shaping, sizing, drying and pasteurizing; integrating dried and shaped ingredient into blended meat extension ingredients; hydrating and blending hydrated ingredient in ground meats; and utilizing aforementioned ingredients in blended plant and mushroom products.

In certain embodiments, provided herein are methods for fermenting filamentous fungi with carbohydrate rich and other raw plant biomass to produce meat-textured ingredients. These methods may entail introduction of plant flour, granules, grains, legumes, or combinations thereof or other plant biomass into the fermentation liquid described herein.

In certain embodiments, provided herein are methods for converting the harvested fungal mycelium into a meat like particulate dry ingredient. In some embodiments, the ingredient is combined with other ingredients for functional enhancement; in some embodiments, the ingredient is used as a stand-alone ingredient; in some embodiments, the ingredient is hydrated with water and integrated into meats; in some embodiments, the ingredient is hydrated and integrated into meat analogues including but not limited to burgers, sausages, patties, nuggets, and more.

In another aspect, provided herein are food compositions comprising a shelf-stable protein food ingredient and one or more meats. In particular embodiments, the food compositions comprise the shelf-stable protein food ingredient in an amount of at least 5% w/w and at least one meat in an amount of at least 10% w/w. Shelf-stable protein food ingredients and useful meats are described in detail in the sections below, along with methods of preparing the food compositions.

In an embodiment, provided herein are methods for processing fungal mycelium described herein into a pasteurized biomass that can be blended into meat to make blended meat products described herein.

DETAILED DESCRIPTION OF PREFERRED EMBODIMENTS

Methods of Production

Figure 1:
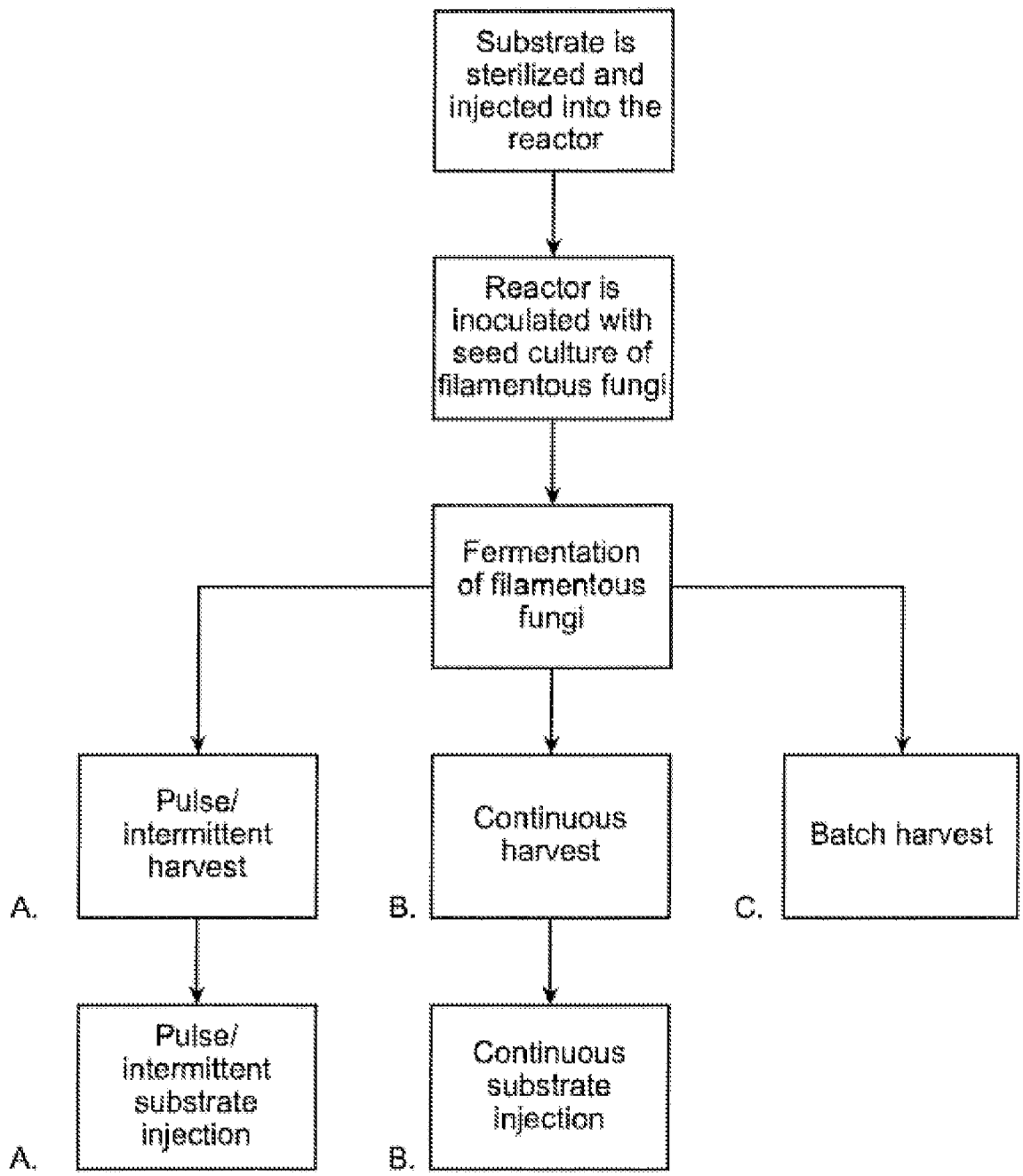
FIG. 1 provides an overview of an embodiment of the fermentation process used to produce the biomass described herein.

In particular embodiments, provided herein are methods for producing shelf-stable protein food ingredients. In certain embodiments, the methods comprise the steps of culturing filamentous fungi in growth medium; harvesting filamentous fungal biomass; optionally, processing the harvested filamentous fungal biomass; optionally, sizing the biomass to form particles; and drying the particles to form the food ingredient. In certain embodiments, the methods comprise the steps of culturing filamentous fungi in growth medium; optionally supplementing the growth medium to form a mixed fungal biomass slurry; harvesting filamentous fungal biomass; optionally, processing the harvested filamentous fungal biomass; optionally supplementing the processed biomass to form a complex ingredient; optionally sizing the biomass to form pieces; and drying the pieces to form the food ingredient.

In the culturing step, the filamentous fungus can be cultured according to standard techniques. The culturing typically comprises growing the filamentous fungus in a growth medium. In certain embodiments, the growth medium comprises hydrolyzed plant biomass byproducts and wastewater streams of the food and beverage industries as well as low-cost plant ingredients and other substrates.

In certain embodiments, the culture is batch culture, fed-batch culture, or continuous culture. The growth medium includes the ingredients described below. Additional additives can be provided according to the judgment of the practitioner in the art. Culture conditions are within the skill of those in the art including culture volume, temperature, agitation, oxygen levels, nitrogen levels, carbon dioxide levels, and any other condition apparent to those of skill.

In certain embodiments, pure oxygen is used in the aeration of the fermentation. Injecting $O_2$ into the downcomer of the reactor can allow maximum interaction with the gas bubbles and substrate while maximizing diffusion of the $O_2$. Pressure swing adsorption (PSA) oxygen concentration is sometimes used to continuously inject $O_2$.

The fungal fermentation can operate with a wide pH range. In certain embodiments the pH is between about pH 2.4 and about pH 8.5, between about pH 3 and about pH 7.5, between about pH 3 and about pH 6.5, between about pH 3 and about pH 5.5, or between about pH 3.5 and about pH 4.5.

The cultured filamentous fungi can be harvested according to any standard technique. The methods include any harvesting technique deemed useful to the practitioner in the art. Useful techniques include centrifugation, pressing, screening, and filtration. In certain embodiments, the filamentous fungi are de-watered and separated by centrifugation. In certain embodiments, the filamentous fungi are de-watered and separated via screw press. In certain embodiments fungi are de-watered and separated via de-watering vibratory screen. In certain embodiments fungi are de-watered via a fluidized bed dryer. In certain embodiments, the filamentous fungi are washed to remove excess growth medium. In certain embodiments, the filamentous fungi are not washed.

In certain embodiments, the harvested filamentous fungal biomass is processed for further use. The processing technique can be any processing technique apparent to the practitioner of skill.

In certain embodiments, hydrolysis and starch conversion process of plant material is accelerated by using a protease, β-glucanase, xylanase, α-amylase and/or other enzymes during the hydrolysis step of generating the substrate of the aerobic fermentation.

In certain embodiments, an alkali or acid treatment is used in the hydrolysis of the plant material used as substrate.

In certain embodiments, the filamentous fungi are sized according to the requirements of the ingredients described herein. Biomass released from de-watering processes can be cake-like as it is similar to fruit, paper, or other pulp upon de-watering. This cake can be broken apart, shredded, chopped, sliced, diced, sieved, and further reduced to desired size using conventional sizing equipment before or after de-hydration. The biomass can be molded, pressed, rolled, extruded, compacted, or manipulated in other ways known to a person with skill in the art of sizing food materials. This can happen before de-watering, during, de-watering, after de-watering, before de-hydration, during de-hydration, or after de-hydration. In certain embodiments, the biomass is sized to yield particles of sizes described below.

In certain embodiments, the biomass slurry comprises highly dispersed filamentous cell structures. Upon removing water using gravity, pressure, compaction, vacuum suction, centrifugation, or other methods known to those skilled in the art of de-watering, filamentous cellular strands interlock with each other to form cohesive filamentous mats that maintain consistency and cohesion. A belt press can be particularly useful in producing large meaty slabs of dense cohesive biomass. These dense mats can be sliced, diced, chopped, molded, folded, extruded, or otherwise manipulated in a way known to a person with skill in the art to form slices, chunks, shreds, nuggets, or other particles and pieces.

In certain embodiments the biomass described herein is extruded using high temperature twin screw extrusion or other extrusion technology to form a material with a more conventional texture that is similar to TVP.

In certain embodiments the biomass of the fermentation process is de-watered to remove moisture from the biomass. The material is optionally pasteurized in the substrate by using steam to heat the biomass slurry to pasteurization temperatures (75-85° C.); the slurry is optionally released into a vibratory screen to de-water the material down to 75-95% water content; the biomass is then optionally pressed with a belt press or screw press or centrifuged to further reduce the water content; the material is then optionally shredded, sized, compacted, molded, otherwise formed, or combinations thereof; the material is then optionally added to a fluidized bed dryer for full dehydration. In particular embodiments, the material is de-watered to yield a water content for the particles as described below.

In certain embodiments the biomass slurry containing 1-8% biomass is released into a belt press system. The material is simultaneously drained and pressed bringing the material down to 60-85% water content. The machine is adjusted to release a cake/slab at a thickness of 1 inch/2.54 cm. The 1 inch slab is continuously conveyed into a spindle and tine mechanical shredder. The shredder releases granular particles in the size range of about 1 mm-about 20 mm.

Particles are continuously sieved using 2 mm and 12 mm sieves. Particles released through the 2 mm sieve are saved and de-hydrated separately or re-introduced to the initial slurry. Particles released through the 12 mm sieve but not through the 2 mm sieve are fed directly into a fluidized bed dryer for dehydration and optionally pasteurization. Particles larger than 12 mm are optionally conveyed back through the shredder for further size reduction. The dehydrated particles between about 2 and about 12 mm are ready for use as a bare ingredient or to be further processed into ingredients described herein. As used herein, the term "about" indicates a reasonable range above and below a unit value, for instance +/−10% or +/1 unit, e.g. mm.

In certain embodiments the biomass slurry is de-watered down to 50-75% water content with methods known to a person with skill in the art of de-watering microbial biomass. The lower moisture biomass at 50-75% water content is then fed through a dough chopping machine. Material is fed through a ¼ inch die and chopped into small particles intermittently by a rotating shear at the end of the die. This results in chunks of a consistent size of about (⅛ inch to ¼ inch) by (⅛ inch to ¼ inch) by (⅛ inch to ¼ inch).

In certain embodiments plant or mushroom materials are added to the biomass prior to de-hydration. These materials can be added to the fungal biomass slurry, the fungal biomass with a water content of 60-85%, the fungal biomass of a water content of 60-75%, the fungal biomass of a water content of 50-75%, the fungal biomass of a water content of 50-65%, or fungal biomass with other water content. These materials may be blended with the fungal biomass described herein and then further de-watered, de-hydrated, or processed into the dried textured ingredients described herein.

In another embodiment supernatant of the fermentation process containing high concentrations of digestive enzymes such as alpha amylase, beta amylase, lipase, and others is processed into side streams. These enzymes can be extracted, purified, and sold or used in pretreatment of hydrolyzed starch rich substrates or in other applications. These enzymes from the supernatant can be integrated into the meat analogues and blends described herein to promote more effective digestion.

Growth Medium

The growth medium can be any growth medium deemed suitable. In particular embodiments, the growth medium comprises plant biomass. In certain embodiments, the plant biomass is a wastewater stream. The plant biomass co-products, ingredients, and wastewater streams can be any material stream deemed suitable to the practitioner of skill in the art. In particular embodiments, the plant biomass is from a low-cost source. In certain embodiments, the plant biomass is a waste stream or a co-product from another food, agriculture, or plant processing process. In such embodiments, the methods provide a second or renewable use of co-products that are conventionally used as farm animal feed, soil enhancement, or discarded entirely. In certain embodiments, the material is selected from ethanol thin stillage, ethanol co-products, rice milling co-products, rice polishings, rice bran, rice process waste water, rice brokens, brewing and distilling spent grains, spent sake rice, spent soy sauce soy, beet pulp, coffee chaff, molasses, sugar refinery waste water, grape pulp, soda production waste water, sugarcane bagasse, sorghum bagasse, or combinations thereof. In preferred embodiments the nutrient streams are potato processing waste-water, ethanol corn stillage, In certain embodiments, the methods comprise fermenting plant ingredients in submerged culture to create cultured plant ingredients that contain a significant concentration of fungal biomass.

In some embodiments, the growth medium comprises one or more plant substrates selected from pea fiber, other plant fibers, gum arabic, natural flavors, texturized pea protein, texturized wheat protein, texturized soy protein, soy protein, wheat starch, wheat protein, pea protein, spices, safflower oil, sunflower oil, olive oil, other oils, oat bran, oat flour, legumes, beans, lentils, lentil powder, bean powder, pea powder, yeast extract, nutritional yeast (immobilized dried yeast), molasses, honey, cane sugar, mushroom powder, white button mushroom powder, shiitake mushroom powder, chickpeas, bamboo fiber, cellulose, isolated oat product, isolated pea product, pea protein, rice protein, fermented rice extract, corn starch, potato starch, kombu extract, algae, potato protein, albumin, pectin, silicone dioxide, food starch, mixed tocopherols (vitamin E), coconut oil, sunflower oil, safflower oil, rapeseed oil, canola oil, dextrose, vegetable glycerin, dried yeast, citrus extract, citrus fiber, beet pulp, beet juice, beet juice extract, turmeric, mushroom extract, shiitake mushroom stems, shiitake mushrooms, white button mushrooms, tofu, soy fiber, soy hydrolysate, yeast extract, seaweed, malted barley, malt extract, yeast extract, whole cell yeast, lentils, black beans, pinto beans, beans, legumes, and any combination thereof. In preferred embodiments, the plant biomass is potato or corn stillage.

In certain embodiments, the growth medium is supplemented with one or more additive components. The additive components might facilitate growth of the filamentous fungi, they might add nutrients to the resulting food product, or they might do both. In certain embodiments, the additive components comprise one or more carbohydrates (simple and/or complex), nitrogen, vitamins, minerals, fats, proteins, or a combination thereof.

In certain embodiments, the additive components comprise one or more oils. In certain embodiments, the one or more oils are selected from the group consisting of grapeseed oil, safflower oil, sunflower oil, olive oil, coconut oil, flaxseed oil, avocado oil, soybean oil, palm oil, canola oil, and combinations thereof.

In certain embodiments, the one or more additives comprise one or more salts. In certain embodiments, the one or more salts consist of elements selected from the group consisting of C, Zn, Co, Mg, K, Fe, Cu, Na, Mo, S, N, P, Ca, Cl, and combinations thereof.

In certain embodiments the salts comprise one or more of the following salts: ammonium nitrate, mono-potassium phosphate, di-potassium phosphate, di-ammonium phosphate, ammonium phosphate, potassium nitrate, magnesium sulfate heptahydrate, calcium chloride dehydrate, zinc sulfate heptahydrate, iron sulfate hexahydrate, copper sulfate pentahydrate, manganese sulfate, and combinations thereof.

In certain embodiments, the growth medium comprises one or more carbohydrates. In certain embodiments the one or more carbohydrates are selected from glucose, sucrose, starch, maltose, and any combination thereof.

In certain embodiments, the growth medium comprises plant oils. The plant oils can significantly increase yields, fermentation efficiency, and fat content of the end material. Non-limiting examples of plant oils can include almond oil, avocado seed oil, cocoa butter, coconut oil, corn oil, cottonseed oil, flax seed oil, grapeseed oil, hemp oil, olive oil, palm kernel oil, peanut oil, pumpkin seed oil, rice bran oil, safflower seed oil, sesame seed oil, sunflower seed oil, soybean oil, or walnut oil.

In certain embodiments, the growth medium comprises vitamins. Useful vitamins include but are not limited to vitamin A, B1, B2, B3, B5, B6, B7 (vitamin H, or Biotin), B9, B12, C, E, D, and K, for the purpose of integrating the vitamin into the end food product via adsorption and cellular integration in the fermentation. In an embodiment, vitamin B12 is added to the fermentation.

In certain embodiments, vitamin B12 is added to the substrate. The vitamin is accumulated by the fungal cells. It is the only B vitamin essential to the human diet that the fungus does not produce on its own.

In certain embodiments the plant-derived biomass or material is added to the growth medium without hydrolysis.

In certain embodiments, the growth medium comprises spent malted barley. The spent malted barley can be used as a plant biomass for hydrolysis, filtration and integration into the substrate as a primary source of carbohydrates, fats, proteins, and micronutrients.

In certain embodiments, the growth medium comprises potato peel. The potato peel can be used as a plant biomass for the hydrolysis, filtration and integration into the substrate as a primary source of carbohydrates, fats, and micronutrients.

In certain embodiments, the growth medium comprises potato processing wastewater. The potato processing wastewater can be used as a primary nutrient source for the fermentation of the fungi. Blanching, starch extraction and other processing methods used for potato processing produce large volumes of nutritionally consistent waste water that is highly effective as a fermentation feedstock.

In certain embodiments waste-water from potato blanching is used as substrate promptly after blanching. The high temperature of the blanching process pasteurizes the substrate, effectively reducing treatment costs in addition to substrate costs. In some embodiments other blanche water and other clean potato processing streams are diverted away from field leaching, conventional treatment methods, and other disposal methods towards the platform described herein.

In certain embodiments, the growth medium comprises beet pulp. The beet pulp can be used as a plant biomass for the hydrolysis, filtration and integration into the substrate as a primary source of carbohydrates, micronutrients, and nitrogen.

In certain embodiments, the growth medium comprises thin stillage (a co-product of biofuel production with corn). The thin stillage can be used as a complex nutrient source of carbon, nitrogen, micronutrients, and fats.

In certain embodiments, the growth medium comprises yeast extract. The yeast extract can be used as a source of nitrogen and micronutrients in the fermentation media.

In certain embodiments, the growth medium comprises filtered beet pulp extract. The filtered beet pulp extract can be used for the primary carbon source.

In certain embodiments, the growth medium comprises potato blanch and processing wastewater. The potato blanch and processing wastewater can be used for the primary nutrient source.

In certain embodiments, the growth medium comprises rice polishings. Rice polishings can be left over from polishing and/or milling rice. They can be used as a plant biomass and added to water, sterilized, and integrated into the reactor as a primary source of carbohydrates, nitrogen, potassium, and other nutrients.

In certain embodiments, the growth medium comprises common carbohydrate sources such as sucrose, glucose, and molasses. They can be used with supplementation for the substrate. These ingredients can be blended, sterilized, and integrated into the reactor with filamentous fungi described herein. The produced biomass can be processed into the versatile dried ingredients described herein.

Filamentous Fungi

The filamentous fungi can be any filamentous fungi deemed suitable to the person of skill in the art.

In certain embodiments, at least one fungus is from the kingdom of Fungi.

In certain embodiments, at least one fungus is from the phylum Basidiomycota, Ascomycota, Glomeromycota, Mucoromycota, or Zoopagomycota.

In certain embodiments, at least one fungus is from the division agaricomycotina, ustilagomycotina, pezizomycotina, saccharomycotina, taphrinomycetes, diversisporalis, archaeosporales, paraglomerales, endogonales, mucorales, mortieralles, entomophthoromycotina, asellariales, kickxellales, dimargaritales, harpellales, zoopagomycotina, or combinations thereof.

In certain embodiments, at least one fungus is from the class tremellomycetes, dacrymycetes, agaricomycetes, exobasisiomycetes, ustilaginomycetes, malasseziomycetes, moniliellomycetes, arthoniomycetes, coniocybomycetes, dothideomycetes, eurotiomyctes, geoglossomycetes, laboulbeniomycetes, lecanoromycetes, leotiomycetes, lichinomycetes, orbiliomycetes, pezizomycetes, sordariomycetes, xylonomycetes, or combinations thereof.

In certain embodiments, at least one fungus is from the order filobasidiales, agaricales, amylocorticiales, atheliales, boletales, jaapiales, lepidostromatales, geastrales, gomphales, hysterangiales, phallales, auriculariales, cantherellales, corticiales, gleophylalles, hymenochaetales, polyporales, russulales, sebacinales, stereopsidales, thelephorales, trechisporales, ceraceosorales, doassansiales, entyomatales, exobasidiales, georgefischeriales, microstromatales, tilletiales, urocystales, ustilaginales, malassezioales, moniliellales, saccharomycetales, coronophorales, glomeralles, Hypocreales, melanosporales, microascales, boliniales, calosphaeriales, chaetospheriales, coniochaetales, diasporthales, magnaporthales, ophiostomatales, sordariales, xylariales, koralionastetales, lulworthiales, meliolales, phylachoralles, trichosphariales, eurotiales, chaetothyriales, pyrenulales, verrucariales, onygenales, mortierellales, mucorales, endogonales, or combinations thereof.

In certain embodiments, at least one fungus is from the family Filobasidium, Dacromycetaceae, Agaricaceae, Amanitaceae, Bolbitiaceae, Broomeiceae, Chromocyphellaceae, Clavariaceae, Cortinariaceae, Cyphellaceae, Enolomataceae, Fistulinaceae, Himigasteraceae, Hydnangiaceae, Hygrophoraceae, Inocybaceae, Limnoperdacea, Lyophyllaceae, Marasmiaceae, Mycenacea, Niaceae, Pellorinaceae, Physalacriaceae, Pleurotacea, Pluteaceae, Porotheleaceae, Psathyrellaceae, Pterulacea, Schizophyllaceae, Stephanosporaceae, Strophariaceae, Tricholomataceae, Typhulaceae, Boletaceae, Boletinellaceae, Coniophoraceae, Diplocystaceae, Gasterellaceae, Gastrosporiaceae, Gomphidiaceae, Gyroporaceae, Hygrophoropsidaceae, Paxillaceae, Protogastraceae, Rhizopogonaceae, Sclerodermataceae, Serpulaceae, Suillaceae, Tapinellaceae, Hymenochaetaceae, Repetobasidiaceae, Schizoporaceae, Cystostereaceae, Fomitopsidaceae, Fragiporiaceae, Ganodermataceae, Gelatoporaceae, Meripilaceae, Merulaciaea, Phenerochaetaceae, Polyporaceae, Sparassidaceae, Steccherinaceae, Xenasmataceae, Albatrellaceae, Amylostereaceae, Auriscalpaceae, Bondarzewiaceae, Echinodontiaceae, Hericiaceae, Hybogasteraceae, Lachnocladiaceae, Peniphoraceae, Russulaceae, Gloeocyctidiellacceae, Stereaceae, Ustilaginomycetes, Saccharomycetaceae, Saccharomycodaceae, Saccharomycopsidaceae, Chaetomiaceae, Lasiosphaeriaceae, Sordariaceae, or combinations thereof.

In certain embodiments, at least one fungus is from the genus *Neurospora, Aspergillus, Trichoderma, Pleurotus, Ganoderma, Inonotus, Cordyceps, Ustilago, Rhizopus, Tuber, Fusarium, Pennicillium, Xylaria, Trametes*, or combinations thereof.

In certain embodiments, at least one fungus is *Aspergillus oryzae, Rhizopus oryzae, Fusarium graminareum, Cordyceps militaris, Cordyceps sinensis, Tuber melanosporum, Tuber magnatum, Pennicillium camemberti, Neurospora intermedia, Neurospora sitophila, Xylaria hypoxion*, or a combination thereof.

Exemplary Methods

In this section, illustrative methods of production are provided. They are intended to exemplify but not limit the methods described above.

In certain embodiments, plant material is soaked in water at 45° C. with 0.75 g/kg alpha-amylase, 0.25 g/kg beta-amylase, 0.5 g/kg beta-glucanase, 0.3 g/kg protease, and 0.3 g/kg xylanase (grams of purified enzyme to kilograms of desiccated substrate). The liquid temperature is increased to 78° C. over the course of 30-180 minutes to activate the enzymes and their hydrolyzing functions. Once the mixture reaches 78° C., where the enzymes are de-activated, the mixture is rapidly brought to 100° C. and maintained there for 10-120 minutes to complete the hydrolysis. The quantities of enzymes, their weights, temperatures, interaction times and their ratios can change based on the plant material being hydrolyzed or to optimize the effect of the enzyme.

In certain embodiments the solid plant-based ingredients are blended into room temperature water. The slurry is pumped through a continuous steam sterilizer and injected into the fermentation reactor described herein at the desired flow rate for the method of fermentation being run. In some embodiments the slurry is pumped at the maximum rate of sterilization to fill a sterile fermenter for the primary initiation of a batch style fermentation. In some embodiments the slurry is injected in pulses aligning with the extraction of biomass slurry described herein. In some embodiments the slurries are injected continuously.

In some embodiments the solid plant-based ingredients are sterilized with standard techniques, known to someone with skill in the art of sterile processes, and introduced to the fermentations of the present inventions.

In some embodiments starch rich processing wastewater from potato blanching, steaming, and/or general processing used as the primary substrate of the fermentation. In some embodiments it is steam sterilized in a continuous media sterilizer. The material may or may not be pre-heated from the potato processing providing energetic efficiency advantages. This material may constitute 100% of the growth media described herein. This material may constitute less than 100% of growth media. In some embodiments the wastewater is supplemented with biotin. In some embodiments this material is supplemented with ammonium gas. In some embodiments this material is supplemented with di-ammonium phosphate. In some embodiments this material is supplemented with ammonium nitrate. In some embodiments this material is supplemented with yeast extract. In some embodiments this material is supplemented with potassium nitrate. In some embodiments this material is supplemented with potassium phosphate. In some embodiments this material is supplemented with calcium chloride. In some embodiments this material is supplemented with magnesium sulfate. In some embodiments this material is supplemented with nitrates. In some embodiments this material is supplemented with ammonium salts. In some embodiments this material is supplemented with the aforementioned plant ingredients described herein. In some embodiments the material is supplemented with aforementioned waste streams or co-products described herein.

In some embodiments the potato processing wastewater chemical oxygen demand (COD) concentration measures between about 500 mg/L and about 300,000 mg/L, between about 2,000 mg/L and about 200,000 mg/L, between about 2,000 mg/L and about 100,000 mg/L, between about 2,000 mg/L and about 50,000 mg/L, between about 2,500 mg/L and about 25,000 mg/L, or between about 2,000 mg/L and about 10,000 mg/L.

In certain embodiments, corn stillage is captured, optionally sterilized, optionally supplemented, and injected into the bioreactors running the fermentations of the present invention. Thin stillage that can be used has an average of 85,000 mg/L COD and about 5,000 mg/L of total nitrogen. This material may constitute 100% of the growth media described herein. This material may constitute less than 100% of growth media. In some embodiments the wastewater is supplemented with biotin. In some embodiments this material is supplemented with ammonium gas. In some embodiments this material is supplemented with di-ammonium phosphate. In some embodiments this material is supplemented with ammonium nitrate. In some embodiments this material is supplemented with yeast extract. In some embodiments this material is supplemented with potassium nitrate. In some embodiments this material is supplemented with potassium phosphate. In some embodiments this material is supplemented with calcium chloride. In some embodiments this material is supplemented with magnesium sulfate. In some embodiments this material is supplemented with nitrates. In some embodiments this material is supplemented with ammonium salts. In some embodiments this material is supplemented with the aforementioned plant ingredients described herein. In some embodiments the material is supplemented with aforementioned waste streams or co-products described herein.

Shelf-Stable Food Ingredient

In another aspect, provided herein are shelf-stable protein food ingredients. The shelf-stable protein food ingredients comprise cultured fungal biomass and a limited amount of water. The shelf-stable protein food ingredients can be prepared according to the methods above. The shelf-stable food ingredients are designed to be a versatile, primarily textured, consistent sized material that is dry, storable, and optimized for ease of use in an end product. Provided herein are exemplary detailed characterizations of the shelf stable protein food ingredients provided herein.

Texture: Texture of the ingredient is important when being used as a meat analogue or a meat extension agent. The filamentous nature of the fungi described herein provides compacted and aligned fibers that mimic muscle in some ways. Texture was analyzed using a rheometer with a 25 mm diameter cylinder probe. The TCP was hydrated for 30 mins at a 1/1.75 w/w ratio of TCP/water. The cross head speed was set to 100 mm/min$^{-1}$ with a max peak stress of 10 kg and a distance between the two supports of 13 mm. The results were averages of 20 treatments.

Chewiness: Chewiness was analyzed using the described methods in "Breene W M, Application of texture profile analysis to instrumental food texture evaluation. *J Texture Stud* 6:53-82 (1975)" using hydrated TCP of the present invention. Chewiness was typically between about 0.5 kg and about 15 kg, between about 1 kg and about 12 kg, between about 2 kg and about 10 kg, or between about 4 kg and about 8 kg.

Cohesiveness: Cohesiveness was determined by taking the dry shelf-stable ingredient of the present invention, hydrating it at a 1/1.75 ratio w/w of dry product to water, treating the material with the following process, and analyzing texture residues. After hydration, the material was subsequently pressurized, dispersed, and dried. Cohesiveness was typically between about 20% and about 90%, between about 30% and about 80%, or between about 40% and about 60%.

Springiness: Springiness was analyzed using the described methods in "Breene W M, Application of texture profile analysis to instrumental food texture evaluation. *J Texture Stud* 6:53-82 (1975)" using hydrated TCP of the present invention. Springiness was typically between about 15% and about 99%, between about 20% and about 85%, between about 40% and about 70%, or between about 40% and about 60%.

Transversal cutting strength: Cutting strength was determined by using a cutting probe (7.5 mm×38.3 mm) with a 2 kg maximum peak stress. Cutting strength helps with determining bite resistance, shear, and texture as it relates to maceration in the human mouth.

Longitudinal cutting strength: Cutting strength was determined by the same methods used for the transversal cutting strength tests.

Protein: The protein content of the ingredients described herein comprise at least 5% total protein. In certain embodiments, the shelf-stable protein food ingredients comprise protein in an w/w amount of 5-100%, 5-75%, 5-50%, 5-45%, 5-40%, 5-35%, 5-30%, 5-25%, 5-20%, or 5-15%. The amino acid profile may comprise of a number of amino acids. Total protein content of an ingredient can be determined by many different methods including but not limited to AOAC International methods 990.03 and 992.15. In some embodiments the ingredient contains the amino acids Methionine, Cystine, Lysine, Phenylalanine, Leucine, Isoleucine, Threonine, Valine, Histidine, Arginine, Glycine, Aspartic acid, Serine, Glutamic acid, Proline, Hydroxyproline, Alanine, Tyrosine, and Tryptophan, Taurine, and others. The ingredient contains all of the essential amino acids for the human diet.

Fat: The fat composition of the ingredient described herein comprises mostly mono- and polyunsaturated fats and can be very low in saturated fats. In some embodiments the total fat content comprises a w/w amount between about 1% and about 80%, between about 1% and about 70%, between about 1% and about 60%, between about 1% and about 50%, between about 2% and about 40%, between about 3% and about 30%, between about 5% and about 30%, between about 6% and about 20%, between about 7% and about 15%, between about 8% and 13%, between about 10% and about 14% by weight of total fat. Fats are primarily monounsaturated and polyunsaturated fats. In some embodiments saturated fats are between 0% and about 40%, between 0% and about 30%, between about 5% and about 20%, and between about 10% and about 20% of the total fat content. In some embodiments unsaturated fats are between about 10% and about 100%, between about 20% and about 100%, between about 30% and about 100%, between about 40% and about 100%, between about 60% and about 90%, or between about 70% and about 80% of the total fat content.

Fiber: In certain embodiments, the shelf-stable protein food ingredients described herein are naturally high in fiber. This can be positive aspect of this type of meat like product. AOAC method 991.43 can be used to determine the fiber content of the ingredients described herein. In some embodiments, fiber content is between about 5% and about 60%, between about 10% and about 50%, between about 15% and about 40%, between about 20% and about 40%, or between about 30% and about 40%.

Vitamins: In certain embodiments, the shelf-stable protein food ingredients comprise a range of water-soluble B vitamins sometimes consisting of thiamin, riboflavin, niacin, pyridoxine, pantothenic acid, folic acid, biotin, and others.

Minerals: In certain embodiments, the shelf-stable protein food ingredients comprise calcium, phosphorous, magnesium, iron, zinc, sodium, manganese and potassium. Calcium is typically in an amount of 200 mg/kg or more. In some embodiments, calcium is between about 500 mg/kg and about 3000 mg/kg, between about 1000 mg/kg and about 2500 mg/kg, between about 1250 mg/kg and about 2000 mg/kg, and between about 1500 mg/kg and 2000 mg/kg. Phosphorous is typically in an amount of 200 mg/kg or more In some embodiments phosphorous is between about 500 mg/kg and about 2500 mg/kg, between about 500 mg/kg and about 2000 mg/kg, between about 750 mg/kg and about 1500 mg/kg, and between about 800 mg/kg and 1200 mg/kg. Potassium is typically in an amount of 100 mg/kg or more. In some embodiments, potassium is between about 1000 mg/kg and about 8000 mg/kg, between about 2000 mg/kg and about 6000 mg/kg, between about 2500 mg/kg and about 5000 mg/kg, and between about 3000 mg/kg and 4500 mg/kg. Sodium is in an amount of 20 mg/kg or more. In some embodiments sodium is between about 20 mg/kg and about 1500 mg/kg, between about 50 mg/kg and about 400 mg/kg, between about 100 mg/kg and about 300 mg/kg, between about 150 mg/kg and about 250 mg/kg, between about 175 mg/kg and about 225 mg/kg. Magnesium is in an amount of 200 mg/kg or more. In some embodiments, magnesium is between about 500 mg/kg and about 3000 mg/kg, between about 1000 mg/kg and about 2500 mg/kg, between about 1250 mg/kg and about 2000 mg/kg, and between about 1500 mg/kg and about 2000 mg/kg. Iron is typically in an amount of 1 mg/kg or more. In some embodiments iron is between about 2 mg/kg and about 100 mg/kg, between about 5 mg/kg and about 80 mg/kg, between about 10 mg/kg and about 50 mg/kg, or between about 20 mg/kg and about 40 mg/kg. Zinc is in an amount of 20 mg/kg or more. In some embodiments zinc is between about 20 mg/kg and about 1500 mg/kg, between about 100 mg/kg and about 600 mg/kg, between about 200 mg/kg and about 500 mg/kg, between about 300 mg/kg and about 500 mg/kg, between about 350 mg/kg and about 450 mg/kg.

Water holding capacity (WHC): In certain embodiments, the shelf-stable protein food ingredients described herein has a WHC significantly higher than that of traditional TVP, that of meat, and that of plant ingredients. WHC is analyzed by fully removing all moisture from the ingredient, weighing the ingredient, then fully hydrating the ingredient, then removing surface moisture, then weighing again. All samples are analyzed in quadruplicate and the average is taken. We have recorded the WHC of the TCP as being as high as 6,743 g/kg. In preferred embodiments the WHC of the TCP ingredient is between about 2,000 g/kg and about 7,000 g/kg. In some embodiments the WHC is between about 2,000 g/kg and about 6,000 g/kg, between about 2,000 g/kg and about 5,000 g/kg, between about 3,000 g/kg and about 5,000 g/kg, between about 3,500 g/kg and about 4,500 g/kg, or between about 4,000 g/kg and about 5,000 g/kg.

Particle size: In certain embodiments, the shelf-stable protein food ingredients are manipulated during the processing of the ingredient to have specific particle sizes. Certain particle sizes work best for certain applications. Particle sizes usually range from a fine powder to 1000 cm sheets. In certain embodiments the particle size is between about 2 mm and about 40 mm, between about 2 mm and about 30 mm, between about 2 mm and about 20 mm, between about 2 mm and about 15 mm, between about 2 mm and about 10 mm, between about 2 mm and about 8 mm, between about 2 mm and about 6 mm, between about 3 mm and about 10 mm, between about 3 mm and about 7 mm, between about 4 mm and about 6 mm, between about 4 mm and about 10 mm, between about 5 mm and about 50 mm, between about 5 mm and about 40 mm, between about 5 mm and about 20 mm, between about 5 mm and about 10 mm, between about 6 mm and about 50 mm, between about 6 mm and about 40 mm, between about 6 mm and about 30 mm, between about 6 mm and about 20 mm, between about 6 mm and about 10 mm, between 6 mm and about 10 mm, between about 7 mm and about 20 mm, between about 7 mm and about 15 mm, between about 7 mm and about 12 mm, between about 7 mm and about 10 mm. In preferred embodiments the particles are 3 mm, 4 mm, 5 mm, 6 mm, 7 mm, 8 mm, 9 mm, 10 mm, 11 mm, and 12 mm.

In some embodiments the particle size is measured with "D-values". D10, D50, and D90 represent the percentage of particles less than a certain sieve size (10%, 50%, and 90% respectively). In particular, D10 indicates a diameter at which 10% of the mass of a sample is in particles less than the indicated diameter. D50 indicates a diameter at which 50% of the mass of a sample is in particles less than the indicated diameter. D90 indicates a diameter at which 90% of the mass of a sample is in particles less than the indicated diameter. In certain embodiments the TCP described herein has a D50 of about 5 mm, a D50 of about 6 mm, a D50 of about 7 mm, a D50 of about 4 mm, a D50 of about 8 mm, a D50 of about 9 mm, a D50 of about 10 mm, a D50 of about 11 mm, a D50 of about 15 mm, a D10 of about 2 mm, a D10 of about 3 mm, a D10 of about 4 mm, a D10 of about 5 mm, a D10 of about 6 mm, a D10 of about 7 mm, a D10 of about 8 mm, a D10 of about 9 m, a D10 of about 10 mm, a D10 of about 11 mm, a D10 of about 12 mm, a D90 of about 2 mm, a D90 of about 50 mesh, a D90 of about 70 mesh, a D90 of about 100 mesh, a D90 of about 1 mm, a D90 of about 2 mm, a D90 of about 3 mm, a D90 of about 4 mm, a D90 of about 5 mm, a D90 of about 6 mm, a D90 of about 7 mm, a D90 of about 8 mm, or a D90 of about 9 mm.

In certain embodiments, the term "about" indicates +/−1 mm. In certain embodiments, the D10, D50, and D90 values are exact, or exact within the tolerance range of the measurement technique. Particle size can be measured according to standard techniques, for instance sieve analysis.

Color: In certain embodiments, the shelf-stable protein food ingredients have a naturally white/off white color. In certain embodiments, the shelf-stable protein food ingredients have an off-white consistent color. In certain embodiments, the shelf-stable protein food ingredients have a tan color. In some embodiments, the material is affected by aforementioned substrate components. Sometimes this color is caramel, red, pink, green, brown, yellow, and other hues. In some embodiments, the color of the shelf-stable protein food ingredients described herein is affected by the plant ingredients that are sometimes combined with the mycelium. Sometimes this color is caramel, red, pink, green, brown, yellow, orange, and other hues.

In some embodiments described herein additional ingredients are integrated into the fermentation process and some concentrations of these additional ingredients remain in the dehydrated product described herein. These supplementary ingredients may alter the nutritional profile, texture, or other properties of the dry ingredients.

In some embodiments, additional ingredients are combined with the shelf-stable protein food ingredients described herein to form a complex ingredient with enhanced functional properties. The ingredients may be selected from the following: pea fiber, other plant fibers, gum arabic, natural flavors, texturized pea protein, texturized wheat protein, texturized soy protein, soy protein, wheat starch, wheat protein, pea protein, spices, safflower oil, sunflower oil, olive oil, other oils, oat bran, oat flour, legumes, beans, lentils, lentil powder, bean powder, pea powder, yeast extract, nutritional yeast (immobilized dried yeast), molasses, honey, cane sugar, mushroom powder, white button mushroom powder, shiitake mushroom powder, chickpeas, bamboo fiber, cellulose, isolated oat product, isolated pea product, pea protein, rice protein, fermented rice extract, corn starch, potato starch, kombu extract, algae, potato protein, albumin, pectin, silicone dioxide, food starch, mixed tocopherols (vitamin E), coconut oil, sunflower oil, safflower oil, rapeseed oil, canola oil, dextrose, vegetable glycerin, dried yeast, citrus extract, citrus fiber, beet pulp, beet juice, beet juice extract, turmeric, mushroom extract, shiitake mushroom stems, shiitake mushrooms, white button mushrooms, tofu, soy fiber, soy hydrolysate, yeast extract and seaweed, natural flavorings, or any combination thereof.

In some embodiments the ingredients described herein is combined with materials known to enhance texture, flavor, palatability, shelf life, stability, and other properties known to people with skill in the art of protein ingredients. These materials can be but are not limited to albumin, pectin, silicone dioxide, zinc gluconate, vitamin B12, maltodextrin, niacin, sodium ascorbate, pyridoxine hydrochloride, tetrasodium pyrophosphate, calcium carbonate, sodium alginate, alginate, trisodium phosphate, calcium acetate, methylcellulose, cellulose, bamboo cellulose, annatto, acetic acid, sodium nitrite, sodium benzoate, soy lecithin, or any combination thereof.

In certain embodiments the shelf-stable protein food ingredient described herein is milled into flour using conventional milling equipment. This flour provides the same nutritional profile aforementioned here while also having properties including but not limited to, gumming properties, tacking properties, enhanced nutrition, high fiber, dough like properties, and other flour like properties that lend themselves to being an effective flour replacement or enhancer. In some embodiments the aforementioned flour is combined with plant based flours such as corn flour, wheat flour, sorghum flour, rye flour, millet flour, *quinoa* flour, and other flours. In some embodiments the aforementioned flour is used in products like a protein bar, bread, pasta, and other flour containing food products.

In some embodiments plant or mushroom biomass is combined with the shelf-stable protein food ingredients described herein. The added properties of the plant/mushroom biomass enhances the product. Such enhancements are but are not limited to color, texture, density, flavor, cooking properties, aesthetics, nutrition, etc. Such plants and mushrooms can be but are not limited to; beet root (*Beta vulgaris*), king oyster mushroom (*Pleurotus eryngii*), oyster mushroom (*Pleurotus ostreatus*), shiitake mushroom (*Lentinula edodes*), or portabello mushroom (*Agaricus bisporus*).

Food Products

In another aspect, provided herein are food products comprising the shelf-stable protein food ingredients. The food products comprise the shelf-stable protein food ingredients and one or more additional food ingredients. In certain embodiments, the shelf-stable protein food ingredients are mixed with fat, carbohydrate, meat, plant, or a combination thereof. In certain embodiments, the shelf-stable protein food ingredients are mixed with plant protein to form food products. In certain embodiments, the shelf-stable protein food ingredients are mixed with meat protein to form food products.

The meat can be any meat deemed suitable by the practitioner of skill. In certain embodiments, the meat is selected from the group consisting of beef, pork, chicken, turkey, lamb, fish, venison, bison, and combinations thereof. In certain embodiments, a shelf-stable protein food ingredient is mixed or layered with beef. In certain embodiments, a shelf-stable protein food ingredient is mixed or layered with pork. In certain embodiments, a shelf-stable protein food ingredient is mixed or layered with chicken. In certain embodiments, a shelf-stable protein food ingredient is mixed or layered with turkey. In certain embodiments, a shelf-stable protein food ingredient is mixed or layered with lamb. In certain embodiments, a shelf-stable protein food ingredient is mixed or layered with fish. In certain embodiments, a shelf-stable protein food ingredient is mixed or layered with crab. In certain embodiments, a shelf-stable protein food ingredient is mixed or layered with lobster. In certain embodiments, a shelf-stable protein food ingredient is mixed or layered with venison. In certain embodiments, a shelf-stable protein food ingredient is mixed or layered with bison.

In certain embodiments, the resulting composition is further mixed with any other food ingredient deemed suitable to the person of skill. In certain embodiments, the additional ingredient is selected from the group consisting of starches, oils, fats, grains, isolates, fibers, plants, algae, mushrooms, and combinations thereof. In certain embodiments, the additional ingredient is selected from the group consisting of pea fiber, other plant fibers, gum arabic, natural flavors, texturized pea protein, texturized wheat protein, texturized soy protein, soy protein, wheat starch, wheat protein, pea protein, spices, safflower oil, sunflower oil, olive oil, other oils, oat bran, oat flour, legumes, beans, lentils, lentil powder, bean powder, pea powder, yeast extract, nutritional yeast (immobilized dried yeast), molasses, honey, cane sugar, mushroom powder, white button mushroom powder, shiitake mushroom powder, chickpeas, bamboo fiber, cellulose, isolated oat product, isolated pea product, pea protein, rice protein, fermented rice extract, corn starch, potato starch, kombu extract, algae, potato protein, albumin, pectin, silicone dioxide, food starch, mixed tocopherols (vitamin E), coconut oil, sunflower oil, safflower oil, rapeseed oil, canola oil, dextrose, vegetable glycerin, dried yeast, citrus extract, citrus fiber, beet pulp, beet juice, beet juice extract, turmeric, mushroom extract, shiitake mushroom stems, shiitake mushrooms, white button mushrooms, tofu, soy fiber, soy hydrolysate, yeast extract and seaweed, natural flavorings, or any combination thereof.

Generally, the food products comprise fungal biomass in an amount of at least 5% w/w. The food products further comprise at least one meat in an amount of at least 10% w/w. In certain embodiments, when more than one meat is present the total amount of meat is at least 10% w/w. Advantageously, the food products can be prepared according to the methods above.

In certain embodiments, the food products comprise at least 5% w/w fungal biomass and at least 10% w/w meat. In certain embodiments, the food products comprise at least 5% w/w fungal biomass and at least 10% w/w meat. In certain embodiments, the food products comprise at least 10% w/w fungal biomass and at least 10% w/w meat. In certain embodiments, the food products comprise at least 15% w/w fungal biomass and at least 10% w/w meat. In certain embodiments, the food products comprise at least 20% w/w fungal biomass and at least 10% w/w meat. In certain embodiments, the food products comprise at least 10% w/w fungal biomass and at least 10% w/w meat. In certain embodiments, the food products comprise at least 25% w/w fungal biomass and at least 10% w/w meat. In certain embodiments, the food products comprise at least 30% w/w fungal biomass and at least 10% w/w meat. In certain embodiments, the food products comprise at least 35% w/w fungal biomass and at least 10% w/w meat. In certain embodiments, the food products comprise at least 40% w/w fungal biomass and at least 10% w/w meat. In certain embodiments, the food products comprise at least 45% w/w fungal biomass and at least 10% w/w meat. In certain embodiments, the food products comprise at least 50% w/w fungal biomass and at least 10% w/w meat.

In certain embodiments, the food products comprise at least 5% w/w fungal biomass and at least 20% w/w meat. In certain embodiments, the food products comprise at least 10% w/w fungal biomass and at least 20% w/w meat. In certain embodiments, the food products comprise at least 20% w/w fungal biomass and at least 20% w/w meat. In certain embodiments, the food products comprise at least 15% w/w fungal biomass and at least 20% w/w meat. In certain embodiments, the food products comprise at least 20% w/w fungal biomass and at least 20% w/w meat. In certain embodiments, the food products comprise at least 20% w/w fungal biomass and at least 20% w/w meat. In certain embodiments, the food products comprise at least 25% w/w fungal biomass and at least 20% w/w meat. In certain embodiments, the food products comprise at least 30% w/w fungal biomass and at least 20% w/w meat. In certain embodiments, the food products comprise at least 35% w/w fungal biomass and at least 20% w/w meat. In certain embodiments, the food products comprise at least 40% w/w fungal biomass and at least 20% w/w meat. In certain embodiments, the food products comprise at least 45% w/w fungal biomass and at least 20% w/w meat. In certain embodiments, the food products comprise at least 50% w/w fungal biomass and at least 20% w/w meat.

In certain embodiments, the food products comprise at least 5% w/w fungal biomass and at least 30% w/w meat. In certain embodiments, the food products comprise at least 10% w/w fungal biomass and at least 30% w/w meat. In certain embodiments, the food products comprise at least 20% w/w fungal biomass and at least 30% w/w meat. In certain embodiments, the food products comprise at least 15% w/w fungal biomass and at least 30% w/w meat. In certain embodiments, the food products comprise at least 20% w/w fungal biomass and at least 30% w/w meat. In certain embodiments, the food products comprise at least 20% w/w fungal biomass and at least 30% w/w meat. In certain embodiments, the food products comprise at least 25% w/w fungal biomass and at least 30% w/w meat. In certain embodiments, the food products comprise at least 30% w/w fungal biomass and at least 30% w/w meat. In certain embodiments, the food products comprise at least 35% w/w fungal biomass and at least 30% w/w meat. In certain embodiments, the food products comprise at least 40% w/w fungal biomass and at least 30% w/w meat. In certain embodiments, the food products comprise at least 45% w/w fungal biomass and at least 30% w/w meat. In certain embodiments, the food products comprise at least 50% w/w fungal biomass and at least 30% w/w meat.

In certain embodiments, the food products comprise at least 5% w/w fungal biomass and at least 40% w/w meat. In certain embodiments, the food products comprise at least 10% w/w fungal biomass and at least 40% w/w meat. In certain embodiments, the food products comprise at least 20% w/w fungal biomass and at least 40% w/w meat. In certain embodiments, the food products comprise at least 15% w/w fungal biomass and at least 40% w/w meat. In certain embodiments, the food products comprise at least 20% w/w fungal biomass and at least 40% w/w meat. In certain embodiments, the food products comprise at least 20% w/w fungal biomass and at least 40% w/w meat. In certain embodiments, the food products comprise at least 25% w/w fungal biomass and at least 40% w/w meat. In certain embodiments, the food products comprise at least 30% w/w fungal biomass and at least 40% w/w meat. In certain embodiments, the food products comprise at least 35% w/w fungal biomass and at least 40% w/w meat. In certain embodiments, the food products comprise at least 40% w/w fungal biomass and at least 40% w/w meat. In certain embodiments, the food products comprise at least 45% w/w fungal biomass and at least 40% w/w meat. In certain embodiments, the food products comprise at least 50% w/w fungal biomass and at least 40% w/w meat.

In certain embodiments, provided herein is a meat analogue from the biomass of *Tuber melanosporum* as a "truffle burger".

In some embodiments the ingredient described herein is combined with seaweed biomass. In certain embodiments the ingredient described herein is combined with algae.

DETAILED DESCRIPTION OF THE FIGURES

FIG. 1 provides an overview of an embodiment of the fermentation process used to produce the biomass described herein Block 1 describes the substrate feedstock used for the fermentation and the injection of said substrate into the reactor post sterilization. The substrate can be a waste stream, plant hydrolysate, plant material, nutrient salts, sugars, starches, fatty acids, proteins, and other nutrients.

Block 2 describes the introduction of the filamentous fungi described herein into the substrate.

Block 3 describes the fermentation parameters described herein.

Blocks 4a. and 5a. describe an optional intermittent substrate introduction and harvesting fermentation operation strategy.

Blocks 4b. and 5b. describe an optional continuous substrate introduction and harvesting fermentation operation strategy.

Block 4c. describes an optional batch fermentation operation strategy.

Figure 2:
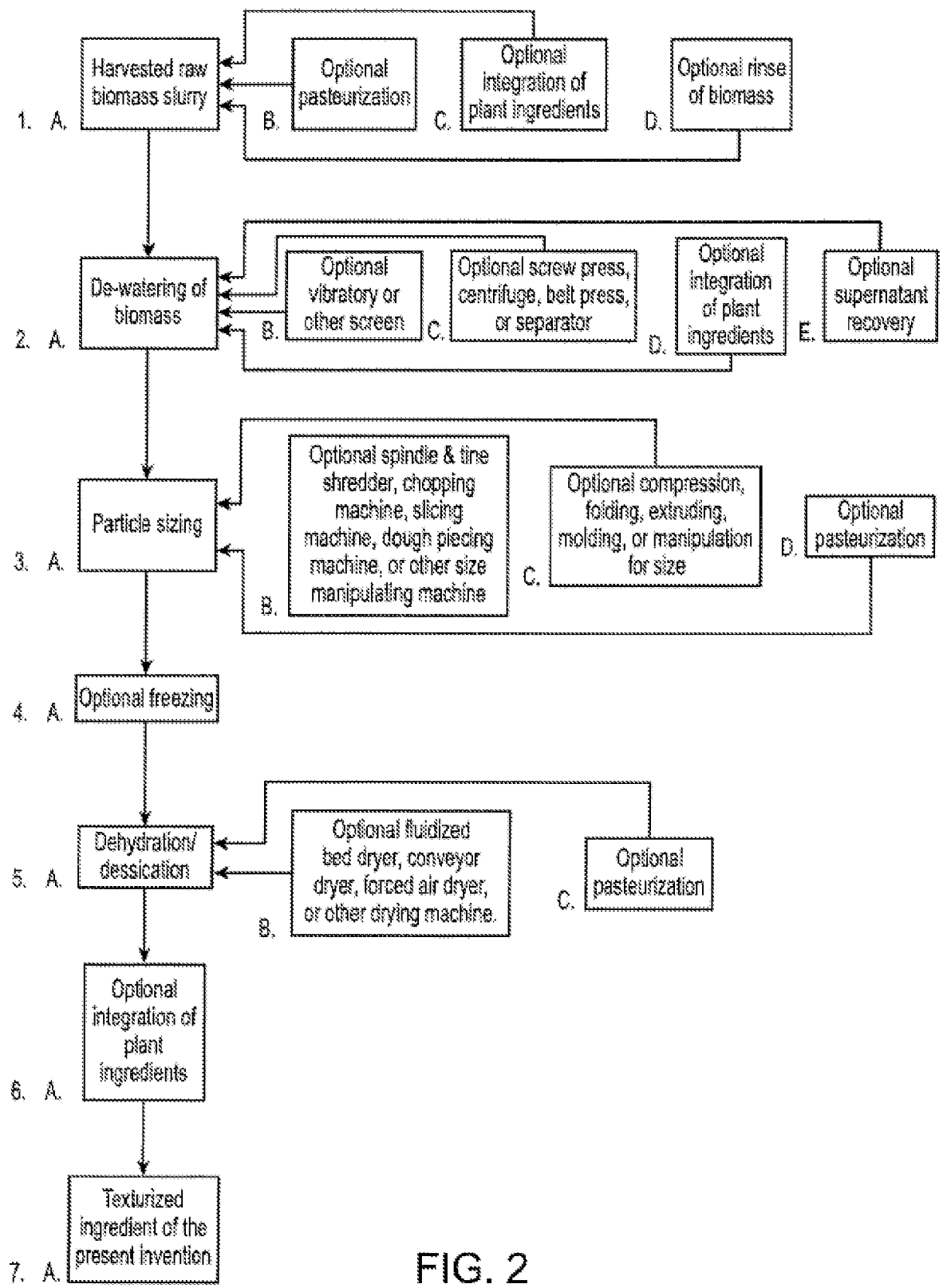
FIG. 2 provides an overview of some methods for processing of the fungal biomass slurry into the textured cultured protein (TCP) described herein.

FIG. 2 provides an overview of some methods for the processing of the fungal biomass slurry into the textured cultured protein (TCP) described herein Blocks 1a.-1d. disclose the raw biomass slurry of the fermentations described herein. The slurry includes but is not limited to biomass fermented with wastewater, co-products, and/or side streams from food and beverage processing, biomass fermented with conventional fermentation substrates, and biomass fermented with plant based ingredients. The biomass may be rinsed to remove residual substrate. The biomass may have the aforementioned plant ingredients integrated at this point. The material may be pasteurized post-harvest from the fermentation.

Blocks 2a.-2e. disclose the steps of processing the biomass to remove moisture via de-watering methods and the option to integrate the plant-based ingredients described herein. The supernatant may optionally be recovered for further purification.

Blocks 3a.-3d. disclose the steps of sizing the particles described herein. Different isolated particle sizes as well as combinations of particle sizes lend themselves to different applications in food products.

Blocks 4a.-5c. disclose optional pasteurization steps where particles and pieces are pasteurized prior to, during, or after dehydration.

Block 4a. describes the optional steps of freezing the pieces of TCP.

Blocks 5a.-5c. disclose the dehydration and desiccation steps for the removal of moisture from the biomass to make the dry and shelf stable ingredient described herein.

Block 6. Discloses the optional combination of other ingredients with the dried pieces to form a composition.

Block 7. discloses the dry ingredient described herein.

Figure 3:
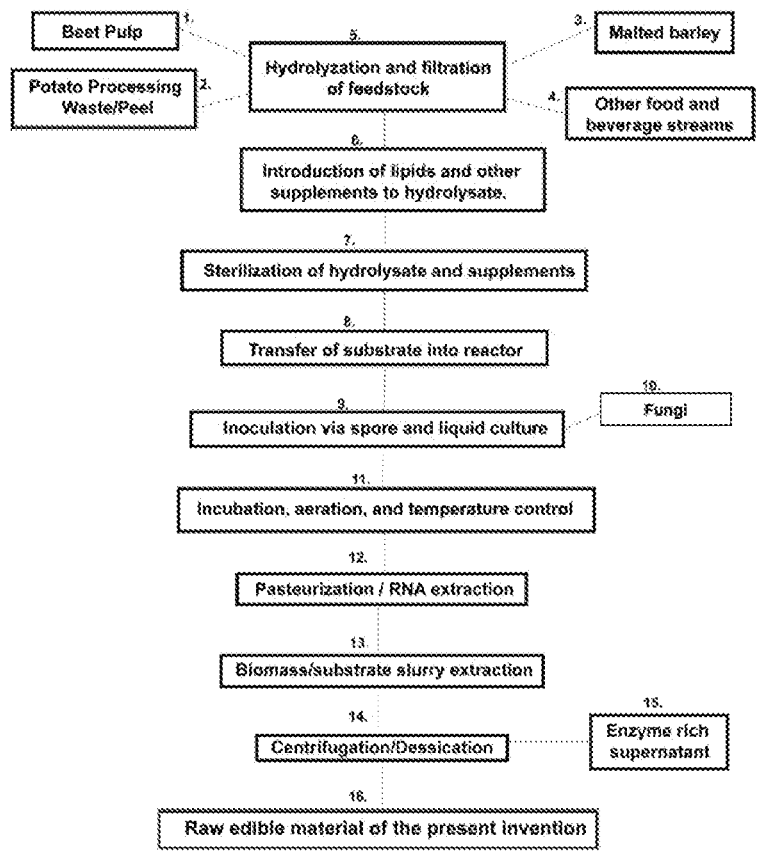
FIG. 3 provides an overview of one embodiment of the fungal biomass fermentation described herein.

FIG. 3 provides an overview of one embodiment of the fungal biomass fermentation described herein Block 1-4 discloses some possible plant materials to be processed into substrate. The plant material can be sourced as waste streams from the food and beverage industries.

Block 5 discloses the step of processing the plant materials into substrate of the fermentation. The plant material is soaked in 100 C water and agitated for 10-120 minutes. The hydrolyzed plant material is separated from the liquid hydrolysate via filtration.

Block 6 discloses the addition of supplements to balance the carbon/nitrogen rations and overall nutritional profile of the substrate. Supplements can be but are not limited to, ammonium phosphate, potassium nitrate, calcium sulfate, glucose, sucrose, or any combination thereof.

Block 7 discloses the requirement of the substrate sterility. The majority of the substrate is heat sterilized, however select ingredients such as the vitamins (for example, vitamin B12 and vitamin B7; (biotin)) are filtered and injected separately.

Block 8 discloses the transfer of the media into the reactor.

Block 9 discloses the methods for inoculation. Liquid seed cultures of mycelium may be transferred into the reactor, high loads of spores can be injected into the substrate, or a volume of biomass/substrate can be in the reactor already, propagated as an inoculum. It is a facet described herein to use fungi of the Phyla Ascomycota and Zygomycota including but not limited to; *Aspergillus oryzae, Rhizopus oryzae, Fusarium graminareum, Cordyceps militaris, Cordyceps sinensis, Tuber melanosporum, Tuber magnatum, Pennicillium camemberti, Neurospora intermedia* or *Xylaria hypoxion*.

Block 10 discloses the addition of a species of fungi as the organism of the fermentation.

Block 11 discloses the fermentation method. Temperature is maintained at 20-34° C., aeration is increased over time using both ambient gas concentrations as well as pure oxygen ranging from 0.03-2 vvm (volume of air per volume of medium per minute). PH is maintained in a state that is ideal for filamentous fungi. 3-8 is the range described herein.

Block 12 discloses the pasteurization of the mycelium. This destroys the viability of the fungus to continue growing and extracts much of the RNA that in undesirable in cellular protein products.

Block 13 discloses the extraction of the biomass and substrate mixture from the bioreactor.

Block 14 discloses the step of de-watering the fungal mycelium. The high moisture retention properties of the mycelium make it necessary to remove some liquid for ideal moisture contents that mimic meat.

Block 15 discloses the remainder of de-watering. This supernatant contains enzymes, acids, lipids, and other valuable extracellular components.

Block 16 discloses the end multi-use fungal biomass material described herein. This is the material that gets used in the blended meats, the blended plant, and the TCP food products.

Figure 4:
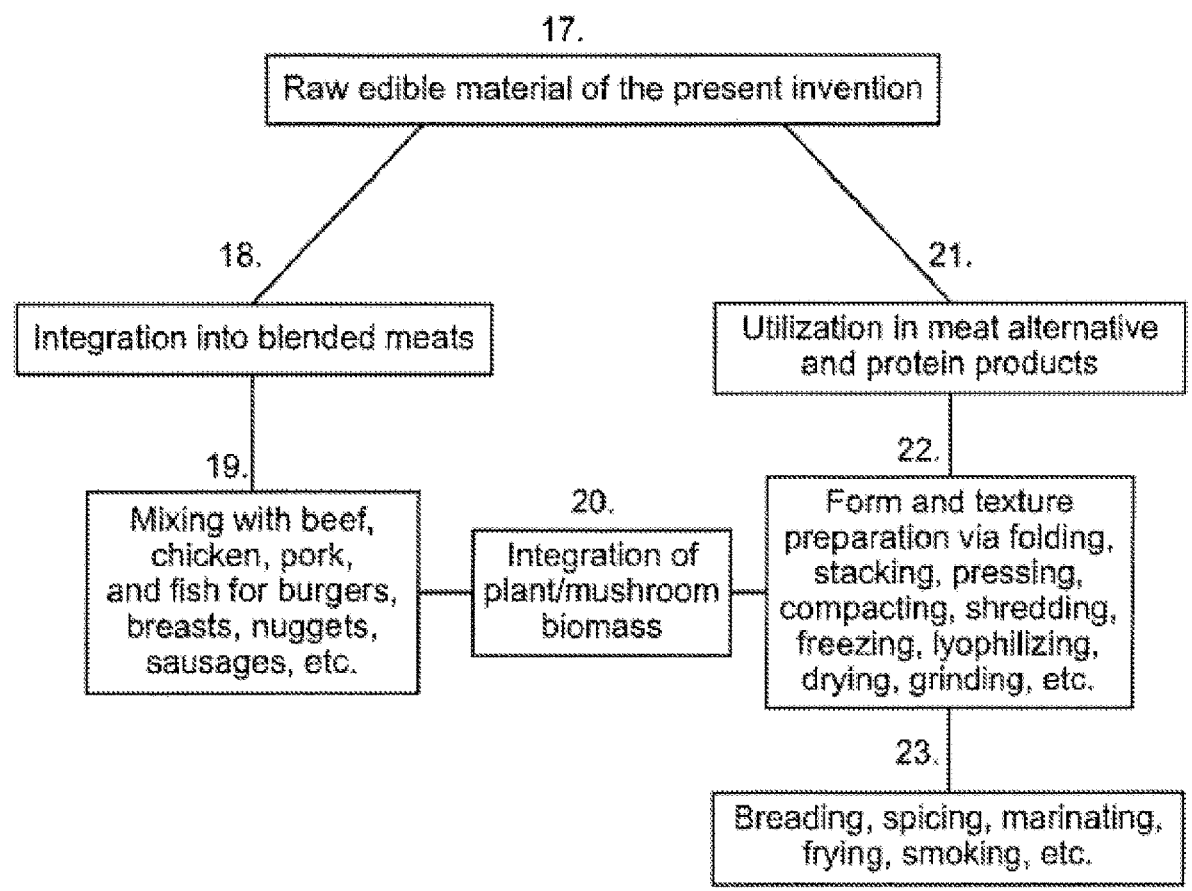
FIG. 4 provides an overview of optional applications of some of the ingredients described herein.

FIG. 4 provides an overview of optional applications of the ingredients described herein Block 17 Discloses the raw food material described herein.

Block 18 disclosed the blending of the fungal biomass into meats to produce hybrid meat/fungi food products.

Block 19 discloses some but not all of the meats and meat products the material is integrated into.

Block 20 discloses the addition of plant and mushroom biomass into the blended fungi/meat products as well as into the fungi based meat alternatives.

Block 21 discloses the use of the material described herein in meat alternative products.

Block 22 discloses some but not all methods for preparation and texturization of the material described herein.

Block 23 discloses some ways in which the meat analogue products are further prepared and cooked.

Figure 5A:
FIGS. 5A and 5B provide photographs of exemplary shelf-stable protein food ingredients provided herein.
Figure 5B:

FIG. 5A provides a close-up photograph on an exemplary TCP provided herein. FIG. 5B provides a photograph of an exemplary TCP provided herein on a serving plate.

EXAMPLES

Below the methods and compositions are further described in examples. These examples are in no way described to limit the present embodiments or their contents.

Example 1

Spores from *Rhizopus oryzae* were plated on agar containing vessels consisting of 15 g/l sucrose, 3 g/l Na3 citrate, 5 g/l KH2PO4, 2 g/l NH4NO3, 0.2 g/l MgSO4, 1 g/l CaSO4, 0.005 g/l Zn SO4, 0.001 g/l Fe(NH4)$_2$(SO4)2, 0.00025 g/l CuSO4, 0.0001 g/l MnSO4, 0.0025 g/l biotin, and 15 g/l agar.

The cultures were incubated at 28° C. for 3 days to encourage maximum sporulation. The air/agar interface supplies aerial hyphae with nutrients embedded in the substrate while exposing hyphae to oxygen. Generous airflow was provided to the culture vessels. The spores were collected in a sterile polypropylene vessel.

The 17 L reactor was prepared by sterilization via 130° C. steam and introducing autoclaved substrate. The reactor substrate consisted of 17 liters DI water, 30 g/l light malt extract prepared from the hydrolyzation and filtration of malted barley, 10 g/l glucose, 5 g/l yeast extract, 0.5 g/l $NH_4H_2NO_3$, 0.2 g/l $MgSO_4$, 3 g/l safflower oil, and 0.0025 g/l biotin.

These spores were then introduced to the 17l reactor at the concentration of 50,000/ml. The reactor was incubated at 29° C. with an increasing aeration starting at 0.1 vvm and reaching 0.8 vvm atmospheric air after 24 hours. The fermentation was complete after 48 hours.

The end substrate/biomass mixture was pressed in a porous cubic frame to de-water the biomass down to 68% for use in aforementioned food products. Samples were taken of the biomass and dried out at 101° C. It was determined via triplicate sampling that the reactor yielded 17 g/l of dry biomass.

Example 2

Aerobic fermentation was carried out in pulse feeding mode. 17l DI water, 30 g/l light malt extract prepared from the hydrolyzation of spent malted barley, 10 g/l glucose, 5 g/l yeast extract, 0.5 g/l $NH_4H_2NO_3$, 0.2 g/l $MgSO_4$, 3 g/l safflower oil, and 0.0025 g/l biotin was autoclaved and added to the sterile reactor. 150 ml of a 2 day old liquid culture of *Cordyceps militaris* mycelium grown on 25 g/l sucrose, 3 g/l Na3 citrate, 5 g/l $KH_2PO_4$, 2 g/l $NH_4NO_3$, 0.2 g/l $MgSO_4$, 1 g/l $CaSO_4$, 0.005 g/l Zn $SO_4$, 0.001 g/l Fe(NH$_4$)$_2$(SO$_4$)$_2$, 0.00025 g/l $CuSO_4$, 0.0001 g/l $MnSO_4$, and 0.0025 g/l biotin. The reactor was maintained at a pH above 4.5 by dripping NaOH and held at 25 C with an increasing ambient air aeration starting at 0.1 vvm and reaching 0.8 vvm after 24 hours. 20 g/l light malt, 10 g/l glucose, and 20 g/l yeast extract was autoclaved and injected into the reactor on hour 48 of the incubation. This substrate supplementation was repeated on hour 96. The growth phase ended on hour 143. The substrate/biomass mixture was pressed in a porous cubic frame and de-watered down to 65% water content. The supernatant was disposed. The pulse feeding strategy yielded 41 g/l of dry biomass.

Example 3

Aerobic fermentation was carried out in pulse feeding/pulse harvest mode. 17 l DI water, 30 g/l potato extract prepared from the hydrolyzation of potato skin, 10 g/l glucose, 2 g/l yeast extract, 0.5 g/l $NH_4H_2NO_3$, 0.2 g/l $MgSO_4$, 3 g/l safflower oil, and 0.0025 g/l biotin was autoclaved and added to the sterile reactor. 50,000 *Aspergillus oryzae* spores/l were added to the substrate. The reactor was maintained at a pH of 4.5 by dripping NaOH into the substrate as needed. The reactor was maintained at 29 C with an increasing ambient air aeration starting at 0.1 vvm and reaching 0.8 vvm after 24 hours. After 48 hours 85% of the substrate biomass mixture was removed. A sterile solution of 14l DI water, 30 g/l potato extract, 10 g/l glucose, 2 g/l yeast extract, 0.5 g/l $NH_4H_2NO_3$, 0.2 g/l $MgSO_4$, 3 g/l safflower oil, and 0.0025 g/l biotin was added filling the reactor back up to almost 17l. The fermentation continued for another 24 hours before the extraction and re-supplementation process was repeated at hour 72. This was then repeated a third time at hour 96. The final harvest of the entire volume of the reactor occurred at hour 120. Biomass was removed and de-watered down to 65% using pressure in a cubic porous frame for further processing into product samples. Biomass yield samplings were carried out in triplicates at each biomass extraction point (hr 48, hr 72, hr 96, and hr 120). Hour 48 had an average of 16.3 g/l dry biomass, hour 72 had an average of 15.7 g/l, hour 96 had an average of 16.1 g/l, and hour 120 had an average of 14.2 g/l.

Example 4

Biomass of *Neurospora intermedia* (500 g) at 80% water content cultured for 72 hours at 29 C with 0.5 v/v/m of aeration in a 300 l internal loop bioreactor at a pH>4.5 on 30 g/l light malt extract, 10 g/l glucose, 20 g/l yeast extract, 0.5 g/l NH$_4$H$_2$NO$_3$, 0.2 g/l MgSO$_4$, 3 g/l safflower oil, and 0.0025 g/l biotin added to a KitchenAid mixer with 50% (w/w) grass fed ground chuck beef (500 g) for a total of 1000 g of meat/mycelium mixture. The mixture was blended on low for 8 minutes until homogenous in texture and color. The mixture was removed and hand pressed into 5 circular patties 1.5" in height×6" in diameter. Two patties were grilled over a propane burner on a "medium" propane flow rate until considered cooked to a point of classification as "medium". Two patties were pan seared on medium heat until slightly blackened and long enough to be considered "medium". Two patties were baked at 425 F for 15 minutes. Two patties were flame cooked over charcoal until they could be considered "medium". Two patties were pan seared until they could be considered "medium rare". One control patty for each cooking method of pure chuck ground beef was cooked in the same fashion as the blended patties as a control.

Example 5

Biomass of *Aspergillus oryzae* (300 g) cultured in supplemented potato hydrolysate was dried in a dehydrator and pulverized into a powder using a mortar and pestle. The powder was mixed with mixed with whole wheat flour (50 g). The mixture was hydrated with 2 cups of whole milk and combined with 3 eggs. The mixture was blended together with ½ stick of butter until malleable dough was created. The dough was rolled into 2" balls and fried. Powdered sugar was added on top of the balls.

Example 6

Asexually sporulating cultures of *Neurospora intermedia* were used to inoculate 8 baffled shaker flasks with a working volume of 200 ml and a 0.2 micron filter patch embedded in the cap. The media contained in the flasks contained 30 g/l sucrose, 3 g/l Na3 citrate, 2 g/l KH2PO4, 2 g/l NH4NO3, 0.2 g/l MgSO4, 1 g/l CaSO4, 0.005 g/l Zn SO4, 0.001 g/l Fe(NH4)2(SO4)2, 0.00025 g/l CuSO4, 0.0001 g/l MnSO4, 0.0025 g/l biotin, and 15 g/l agar agar. These flasks were incubated and agitated for 24 hours at 100 rpm and 29° C. on a incubated shaker table.

A 100 liter internal loop airlift bioreactor (ILAB) was filled to an 80 L working volume with DI water. Using a magnetically coupled agitator for agitation, 45 g/L potato flour, 2 g/L yeast extract, 0.5 g/L NH$_4$H$_2$NO$_3$, 0.0025 g/l biotin was successively added to the vessel until homogenous. The media was sterilized with steam in place methods (125° C. for 20 minutes). The eight 24-hour old baffled flask starter cultures were aseptically injected into the 100 L reactor. The reactor was maintained at 31° C. The reactor was maintained at a pH of 4.5 by dripping NaOH into the substrate as needed. Compressed air was injected through a sintered steel sparger with a porosity of 0.2 microns in the riser section of the ILAB at a flow rate of 0.1 vvm. The flow rate was increased to 1.0 vvm over the first 48 hours.

These conditions were maintained for 72 hours.

The biomass slurry was filtered using nylon mesh filter sacks to remove the supernatant leaving a high moisture biomass. The high moisture biomass was centrifuged to further reduce the moisture content down to 75%. The reduced moisture biomass was shredded into particles less than 0.25" by using a shaft mounted 5 blade shredder at 500 rpm. Particles were sieved to separate the particle sizes. Particles were dehydrated at 50° C. for 120 minutes until bone dry with a moisture content of 4%. The material was packaged and stored.

Example 7

A 48 hour old fermentation operating in a 100 L internal loop airlift bioreactor with *Neurospora crassa* biomass and 30 g/l sucrose, 3 g/l Na3 citrate, 2 g/l KH2PO4, 2 g/l NH4NO3, 0.2 g/l MgSO4, 1 g/l CaSO4, 0.005 g/l Zn SO4, 0.001 g/l Fe(NH4)2(SO4)2, 0.00025 g/l CuSO4, 0.0001 g/l MnSO4, 0.0025 g/l biotin was injected, via peristaltic pumping, with 10 g/l of powdered dried oats that had been steam sterilized in four, 1 liter glass bottles with DI water adjusted to the one liter mark on each bottle. The fermentation was continued with the previous conditions for a remaining 8 hours. The material was harvested and processed with typical methods.

Example 8

The dry TCP described herein was fully characterized in its nutritional profile and texture. The TCP was cultivated in a 100 L internal loop airlift bioreactor for 3 days at 31 C with 0.7 VVM of compressed air and 40 g/l sucrose, 3 g/L sodium citrate, 3.5 g/L ammonium phosphate, 1.3 g/l potassium nitrate, 0.1 g/l magnesium sulfate, 0.05 g/l calcium chloride and minor amounts of copper, iron, manganese, and zinc. The material was harvested in slurry form, de-watered down to 75% WC using a vibratory screen and screw press, compacted into a dense block, shredded with a spindle and tine shredding device, sized with a 5 mm mesh, and dehydrated with a forced air conveyor dryer. The material was baked at 83 C in a convection oven for 15 minutes for a final pasteurization. The material with an ambient hydration of 4.3% water content (WC) was analyzed for a full nutritional profile via triplicate sampling. The following are averages. Using AOAC method 991.43, fiber content was determined to be 18.14%. Using AOAC method 990.03 total protein was determined to be 53%. Using AOAC method 945.44 total fat was determined to be 9.02%. Using AOAC methods for individual amino acids the following concentrations were determined: Methionine 0.53%, Cystine 0.47%, Lysine 2.49, Phenylalanine 1.35%, Leucine 3.02%, Isoleucine 1.53%, Threonine 1.79%, Valine, 2.84%, Histidine 1.61%, Arginine 3.07%, Glycine 1.52%, Aspartic acid 3.91%, Serine 1.74%, Glutamic acid 5.78%, Proline 1.44%, Hydroxyproline 0.04%, Alanine 2.51%, Tyrosine 2.17%, and Tryptophan 0.42%, Taurine 0.01%. AOAC method 2012.13 was used to determine the fatty acid profile which was determined to be (relative %): Total omega 3 content 3.3%, total omega 6 content 35.9%, total omega 9 content 38.3%, total saturated 17.8%, total monounsaturated 42.7%, and total polyunsaturated 39.3%. Using AOAC method 990.12 the aerobic plate count was determined to be <10,000 cfu/g. Using AOAC method 997.02 the mold and yeast count was determined to be <200 CFU/g. Using AOAC method 991.14 the *E. coli* levels were determined to be <10/g. Using AOAC method 2003.09 the *Salmonella* spp. Was determined to be negative in 375 grams of TCP.

The aforementioned TCP was then characterized in its texture and macro-scale characteristics after hydration. Color was visually determined to be an off white/tan. Particle size was determined to be an average of 5 mm on the x, y, and z planes. Water absorption capacity (WAC) was determined to be 4624.77 g/kg. The chewiness, cohesiveness, springiness, as well as transversal and longitudinal cutting strength were analyzed to determine "texture". The chewiness was determined to be 3.43 kg. The cohesiveness was determined to be 45%. The springiness was determined to be 62%. Transversal cutting strength was determined to be 12,408 kg/m$^{-2}$. Longitudinal cutting strength was determined to be 11,316 kg/m$^{-2}$. These numbers were compared to results from beef, chicken, and pork.

Example 9: Blended Beef/TCP Patties 60 g Immobilized TCP of *Rhizopus oryzae* Hydrated at 72% Water Content/60 g Ground Chuck Beef Fungal biomass was hydrated and added to the ground beef after the initial course grind. The components were then mixed/blended into the desired consistency for burger patties.

The ground beef/fungi blend was packed into a circular mold with a diameter of 120 mm.

The patty was cooked in an oiled pan on medium heat until internal temperature reached 73 C.

Example 10: Blended Chicken/TCP Breaded Nuggets 70 g Immobilized TCP of *Aspergillus oryzae* Hydrated at 65% Water Content/30 g Ground White Meat Chicken Fungal TCP was hydrated and added to shredded chicken breast meat. The mixture was tossed and ground through plates with ⅛" holes.

Meat blend was scooped into 10 gram nuggets. The nuggets were compressed into a breading consisting of 80% whole wheat flower, 18.3% bread crumbs, 0.6% salt, 0.2% paprika, 0.2% basil, 0.2% cayenne pepper, 0.2% garlic powder, 0.3% ground black pepper by dry weight. Compression was applied to both sides of the nugget, simultaneously covering the entire meat blend and flattening the nugget on two sides.

Nuggets were fried in ¼" depth peanut oil until breading was crispy.

Example 11: Blended Pork/TCP Sausages 130 g Immobilized TCP of *Neurospora intermedia* Hydrated at 68% Water Content/80 g Ground Pork/30 g Pork Fat TCP was hydrated and added to ground pork and fat mixture. Contents were mixed with 0.2 g salt, 0.05 g powdered sage, 0.1 g ground black pepper, 0.2 g Italian herbs, 0.1 g paprika. Mixture was mixed together using a mechanical mixer for 4 minutes. Mixture was put through a grinder with ⅛" holes.

Ground and blended material was injected into a cleaned and prepared natural hog sausage casing and tied off to close. The sausage was twisted and cut to produce two sausage links.

Links were pan seared in a pan on medium heat until center temperature reached 71 C.

Example 12: Dry Chicken Extender 80 g of Immobilized *Neurospora sitophila* TCP at 6% Water Content Raw mycelium was harvested and de-watered down to 70% water content using a screen and screw press. This material was shredded, sized into 5 mm particles, and consecutively dried down to 6% water content. This TCP was then baked in an oven at 85° C. for 15 minutes for a final pasteurization. 80 g of the TCP was mixed and coated with 10 g safflower oil, 5 g algae, 5 g natural chicken flavoring.

The composition had particle sizes of 3-10 mm. The plant based ingredients adhered evenly to the surfaces of the dehydrated mycelium particles. The mixture had a tan color and tasted like dry chicken.

The composition was hydrated at a 1/1.5 ratio of dry material to water by weight. This hydrated material was mixed at a 30/70% ratio of composition to ground chicken in a mixer until texturally homogenous (roughly 30 seconds). The blended chicken was formed into patties and cooked in the same way as chicken patties.

Example 13: Dry Pork Extender 72 g of Immobilized *Neurospora intermedia* TCP at 5.5% Water Content Raw mycelium was harvested and de-watered down to 70% water content using a screen and screw press. This material was shredded, sized into 5 mm particles, and consecutively dried down to 6% water content. This TCP was then baked in an oven at 85° C. for 15 minutes for a final pasteurization. 72 g of the TCP was mixed and coated with 10 g safflower oil, 2 g yeast extract, 6 g bamboo fiber, 10 g natural pork flavoring.

The composition had particle sizes of 3-10 mm. The plant-based ingredients adhered evenly to the surfaces of the dehydrated mycelium particles. The mixture had a tan color and tasted like dry pork.

The composition was hydrated at a 1/1.5 ratio of dry material to water by weight. This hydrated material was mixed at a 30/70% ratio of composition to ground pork in a mixer until texturally homogenous (roughly 30 seconds). The blended pork was formed into sausage links and cooked in the same way as pure pork sausages.

Example 14: Dry Beef Extender 64 g of Immobilized *Neurospora crassa* TCP at 6% Water Content Raw mycelium was harvested and de-watered down to 70% water content using a screen and screw press. This material was shredded, sized into 5 mm particles, and consecutively dried down to 6% water content. This material was then baked in an oven at 85° C. for 15 minutes for a final pasteurization. 64 g of the material was mixed and coated with 10 g safflower oil, 2 g yeast extract, 5 g psyllium husk, 10 g beet pulp powder, 10 g natural beef flavoring.

The composition had particle sizes of 3-10 mm. The plant-based ingredients adhered evenly to the surfaces of the TCP particles. The mixture had a tan color and tasted like dry beef.

The composition was hydrated at a 1/1.5 ratio of dry material to water by weight. This hydrated material was mixed at a 30/70% ratio of composition to ground beef in a mixer until texturally homogenous (roughly 30 seconds). The blended beef was formed into burger patties and cooked in the same way as pure beef burgers.

Example 15: Dry Chicken Extender 80 g of Immobilized *Neurospora sitiphila* TCP at 6% Water Content Raw mycelium was harvested and de-watered down to 70% water content using a screen and screw press. This material was shredded and consecutively dried down to 6% water content. This material was then baked in an oven at 85° C. for 15 minutes for a final pasteurization. 80 g of the TCP was mixed and coated with 10 g safflower oil, 5 g algae, 5 g natural chicken flavoring.

The composition had particle sizes of 3-10 mm. The plant based ingredients adhered evenly to the surfaces of the TCP particles. The mixture had a tan color and tasted like dry chicken.

The composition was hydrated at a 1/1.5 ratio of dry material to water by weight. This hydrated material was mixed at a 30/70% ratio of composition to ground chicken in a mixer until texturally homogenous (roughly 30 seconds). The blended chicken was formed into patties and cooked in the same way as chicken patties.

Example 16: Dry Pork Extender 72 g of Immobilized *Neurospora intermedia* at 5.5% Water Content Raw mycelium was harvested and de-watered down to 70% water content using a screen and screw press. This material was shredded and consecutively dried down to 6% water content. This material was then baked in an oven at 85° C. for 15 minutes for a final pasteurization. 72 g of the TCP was mixed and coated with 10 g safflower oil, 2 g yeast extract, 6 g bamboo fiber, 10 g natural pork flavoring.

The composition had particle sizes of 3-10 mm. The plant based ingredients adhered evenly to the surfaces of the TCP particles. The mixture had a tan color and tasted like dry pork.

The composition was hydrated at a 1/1.5 ratio of dry material to water by weight. This hydrated material was mixed at a 30/70% ratio of composition to ground pork in a mixer until texturally homogenous (roughly 30 seconds). The blended pork was formed into sausage links and cooked in the same way as pure pork sausages.

Example 17: Dry Beef Extender 64 g of Immobilized *Neurospora crassa* at 6% Water Content Raw mycelium was harvested and de-watered down to 70% water content using a screen and screw press. This material was shredded and consecutively dried down to 6% water content. This material was then baked in an oven at 85° C. for 15 minutes for a final pasteurization. 64 g of the material was mixed and coated with 10 g safflower oil, 2 g yeast extract, 5 g psyllium husk, 10 g beet pulp powder, and 10 g natural beef flavoring.

The composition had particle sizes of 3-10 mm. The plant-based ingredients adhered evenly to the surfaces of the TCP particles. The mixture had a tan color and tasted like dry beef.

The composition was hydrated at a 1/1.5 ratio of dry material to water by weight. This hydrated material was mixed at a 30/70% ratio of composition to ground beef in a mixer until texturally homogenous (roughly 30 seconds). The blended beef was formed into burger patties and cooked in the same way as pure beef burgers.

Example 18: Focus Group on TCP in Blended Meat Application

The dry shelf-stable ingredient of the present invention with a D-50 of 4 mm at 75% w/w was coated in safflower oil at 10% w/w and blended with "brown chicken" natural flavor (Fontana Flavors) at 10% w/w as well as pea fiber at 5% w/w. The coated particles were hydrated at a ½ ratio of particles/water w/w (200% hydration) and left to soak for 25 minutes. The hydrated TCP was mixed with ground chicken meat at a 50/50 ratio w/w. The blend was formed into 16 g nuggets, then breaded in a standard nugget breading consisting of rice flour, wheat flour, cornmeal, and spices.

Pure ground chicken was formed into 16 g nuggets and breaded with the exact same breading formula. Both the pure chicken and the blended nuggets were fried until they floated in the oil and had a golden crispy breading. The products were kept separate, given the respective ID's of 1776 for fully chicken and 1865 for the blended nugget.

20 random testers were selected from a bank of participants unfamiliar to the project. They were requested to taste the two samples and to record their preference using three options; "X preferred" or "cannot tell the difference". The testers were served each sample with a short break in between. Their results were recorded.

12 said they could tell no difference. 6 preferred the blended nugget, and 2 preferred the fully meat nugget. (60% said no difference, 30% preferred the blended nugget, 10% preferred the full chicken nugget).

Example 19: Treatment Efficiency with Potato Processing Wastewater

Cultures of *Neurospora sitophila* were cultured in two 200 ml baffled shaker flasks with house media for 30 hours at 100 RPM and 31 C. Media was prepared in agitated 100 L pressure vessels and steam sterilized to prepare 16 L of media. The media consisted of potato processing waste water generated from the blanching of potatoes for french fry production. The water contained a high COD of 37,304 mg/L COD, 2.34% TSS, 1397 mg/L TN, 3.5% sugars, as well as phosphate and sulphate. The media was supplemented with 1 g/L yeast extract, 0.5 g/L ammonium nitrate, and 10 ml of vegetable oil based antifoam. The media was steam sterilized and injected into the steam sterilized 17 L reactor. The seed cultures (400 ml total) were added to the reactor. The fermentation was maintained at 31 C, a pH of 4.5 and 0.8 vvm of compressed air for three days (72 hours). The material was harvested and processed as typical with the methods of the present invention.

The supernatant was analyzed. Remaining COD was 1283 mg/L, TSS was 0.01%, TN was 188 mg/L and sugars was 0%. The treatment was highly effective in reducing COD as well as TSS and TN. In addition to creating a quality TCP from the process, the treatment capacity of the platform proves viable as a treatment to the potato processing waste.

What is claimed is:

1. A method of producing a meat analogue food product from a filamentous fungal mycelium, wherein the method comprises:
    a) culturing a filamentous fungus from the genus *Neurospora* in a liquid growth medium to produce a filamentous fungal biomass slurry comprising about 0.5-8% biomass;
    b) harvesting the filamentous fungal biomass slurry and dewatering the filamentous fungal biomass slurry to produce a harvested filamentous fungal biomass comprising about 60-85% water and about 15-40% filamentous fungal biomass;
    c) dewatering the harvested filamentous fungal biomass to produce a filamentous fungal biomass cake;
    d) producing filamentous particles from the filamentous fungal biomass cake and drying the filamentous particles;

e) sizing the dried filamentous particles to comprise a mean particle size between about 5 mm and about 50 mm; and f) hydrating the sized dried filamentous particles at about 30% to about 70% water content to form the meat analogue food product.

2. The method of claim 1, comprising drying the filamentous particles to about 4% to about 6% water.

3. The method of claim 1, comprising drying the filamentous particles at about 50° C. to about 100° C.

4. The method of claim 1, comprising sizing the dried filamentous particles to comprise a mean particle size between about 5 mm and about 20 mm.

5. The method of claim 1, wherein the harvested filamentous fungal biomass is pasteurized before drying.

6. The method of claim 1, further comprising pasteurizing the meat analogue food product.

7. The method of claim 1, further comprising shaping the meat analogue food product into patties, nuggets, balls, or sausage links.

8. The method of claim 1, further comprising mixing or layering the meat analogue food product with a meat to produce a meat blended food product.

9. The method of claim 8, wherein the meat analogue food product is ground into a flour before mixing or layering with the meat.

10. The method of claim 8, wherein the meat is selected from the group consisting of beef, pork, chicken, turkey, fish, lamb, crab, lobster, venison, bison, and combinations thereof.

11. The method of claim 8, wherein the meat blended food product comprises at least about 5% weight per weight (w/w) of the meat analogue food product and at least about 10% w/w of the meat.

12. The method of claim 1, further comprising combining the meat analogue food product with plant ingredients.

13. The method of claim 1, further comprising combining the meat analogue food product with one or more natural flavorings.

14. The method of claim 13, wherein the one or more natural flavorings is a natural chicken flavoring, a natural beef flavoring, or a natural pork flavoring.

15. The method of claim 1, wherein the meat analogue food comprises protein in an amount of 5-100% w/w, 5-75% w/w, 5-50% w/w, 5-45% w/w, 5-40% w/w, 5-35% w/w, 5-30% w/w, 5-25% w/w, 5-20% w/w, or 5-15% w/w.

16. The method of claim 1, wherein the liquid growth medium comprises 10-30 g/l sucrose or glucose, 2.0-5.0 g/l $KH_2PO_4$, or 0.5-2.0 g/l $NH_4NO_3$.

17. The method of claim 1, wherein the liquid growth medium components are derived from brewing byproducts, brewing spent grains, fruit pulp, grain processing, distillation byproducts, distillation spent grains, corn stillage, potato processing waste, potato blanche water, rice processing waste, wheat straw, dairy whey, coffee processing waste, soda manufacturing waste, molasses, sugarcane bagasse, vinasse, cassava processing waste, or any combination thereof.

18. The method of claim 17, wherein one or more of the liquid growth medium components are derived from brewing byproducts or brewing spent grains.

19. The method of claim 1, wherein the filamentous species are *Neurospora intermedia, Neurospora sitophila, Neurospora crassa*, or a combination of *Neurospora intermedia, Neurospora crassa*, and *Neurospora sitophila*.

20. A method of producing a meat analogue food product from a filamentous fungal mycelium, wherein the method comprises:

a) providing a shelf-stable protein food ingredient comprising: filamentous fungal particles from the genus *Neurospora* with a mean particle size between about 5 mm and about 50 mm, said filamentous fungal particles consisting essentially of cultured filamentous fungal biomass from the genus *Neurospora* in an amount at least about 94-96% w/w; and water in an amount of about 4% to about 6% w/w; and b) hydrating the shelf-stable protein food ingredient to between about 30% to 70% water content to form the meat analogue food product.

21. The method of claim 20, further comprising pasteurizing the meat analogue food product.

22. The method of claim 20, further comprising shaping the meat analogue food product into patties, nuggets, balls, or sausage links.

23. The method of claim 20, further comprising mixing or layering the meat analogue food product with a meat to produce a meat blended food product.

24. The method of claim 23, wherein the meat analogue food product is ground into a flour before mixing or layering with the meat.

25. The method of claim 23, wherein the meat is selected from the group consisting of beef, pork, chicken, turkey, fish, lamb, crab, lobster, venison, bison, and combinations thereof.

26. The method of claim 23, wherein the meat blended food product comprises at least about 5% w/w of the meat analogue food product and at least about 10% w/w of the meat.

27. The method of claim 20, further comprising combining the meat analogue food product with plant ingredients.

28. The method of claim 20, further comprising combining the meat analogue food product with one or more natural flavorings.

29. The method of claim 28, wherein the one or more natural flavorings is a natural chicken flavoring, a natural beef flavoring, or a natural pork flavoring.

30. The method of claim 20, wherein the meat analogue food comprises protein in an amount of 5-100% w/w, 5-75% w/w, 5-50% w/w, 5-45% w/w, 5-40% w/w, 5-35% w/w, 5-30% w/w, 5-25% w/w, 5-20% w/w, or 5-15% w/w.

31. The method of claim 20, wherein the filamentous species are *Neurospora intermedia, Neurospora sitophila, Neurospora crassa*, or a combination of *Neurospora intermedia, Neurospora crassa*, and *Neurospora sitophila*.

32. A food product comprising:

a) filamentous fungal particles from the genus *Neurospora* with a mean particle size between about 5 mm and about 50 mm in an amount of at least about 5% w/w, and water in the amount of about 4% to about 6%; and b) a food ingredient in an amount of at least about 10% w/w.

33. The food product of claim 32, wherein the food product comprises about 5-50% w/w of the fungal particles, and about 10-40% w/w of the food ingredient.

34. The food product of claim 32, wherein the food product comprises protein in an amount of 5-100% w/w, 5-75% w/w, 5-50% w/w, 5-45% w/w, 5-40% w/w, 5-35% w/w, 5-30% w/w, 5-25% w/w, 5-20% w/w, or 5-15% w/w.

35. The food product of claim 32, wherein the food product comprises fat in an amount of 1-80%.

36. The food product of claim 32, wherein the fungal particles are selected from the species of *Neurospora intermedia, Neurospora sitophila, Neurospora crassa*, or a combination of *Neurospora intermedia, Neurospora crassa*, and *Neurospora sitophila*.

37. The food product of claim 32, wherein the mean particle size of the fungal particles is between about 5 mm and about 20 mm.

38. The food product of claim 32, further comprising albumin, pectin, silicone dioxide, zinc gluconate, vitamin B12, maltodextrin, niacin, sodium ascorbate, pyridoxine hydrochloride, tetrasodium pyrophosphate, calcium carbonate, sodium alginate, alginate, trisodium phosphate, calcium acetate, methylcellulose, cellulose, bamboo cellulose, annatto, acetic acid, sodium nitrite, sodium benzoate, soy lecithin, natural flavorings, or any combination thereof.

39. The food product of claim 32, wherein the food ingredient comprises:
   a) one or more meat ingredients;
   b) one or more plant ingredients; or
   c) both one or more meat ingredients and one or more plant ingredients.

40. The food product of claim 39, wherein the food ingredient further comprises water and the one or more meat ingredients.

41. The food product of claim 39, wherein the food ingredient further comprises the one or more meat ingredients.

42. The food product of claim 32, wherein the food ingredient further comprises about 30% to about 70% water content.

43. The food product of claim 39, wherein the one or more meat ingredients is selected from the group consisting of beef, pork, chicken, turkey, fish, lamb, crab, lobster, venison, bison, and combinations thereof.

44. The food product of claim 32, wherein the food product is in the shape of a patty, nugget, ball, or sausage link.

45. The food product of claim 32, further comprising one or more natural flavorings.

46. The food product of claim 45, wherein the one or more natural flavorings is a natural chicken flavoring, a natural beef flavoring, or a natural pork flavoring.

* * * * *